(12) United States Patent
Ueno

(10) Patent No.: US 8,865,898 B2
(45) Date of Patent: Oct. 21, 2014

(54) NUCLEOSIDE ANALOG OR SALT THEREOF, OLIGONUCLEOTIDE ANALOG, GENE EXPRESSION INHIBITOR, AND NUCLEIC-ACID PROBE FOR DETECTING GENE

(75) Inventor: Yoshihito Ueno, Gifu (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 13/990,649

(22) PCT Filed: Nov. 30, 2011

(86) PCT No.: PCT/JP2011/077684
§ 371 (c)(1),
(2), (4) Date: Aug. 28, 2013

(87) PCT Pub. No.: WO2012/074012
PCT Pub. Date: Jun. 7, 2012

(65) Prior Publication Data
US 2014/0221637 A1    Aug. 7, 2014

(30) Foreign Application Priority Data

Nov. 30, 2010 (JP) ................... 2010-267314
Aug. 31, 2011 (JP) ................... 2011-190048

(51) Int. Cl.
| | | |
|---|---|---|
| C07D 239/95 | (2006.01) | |
| C07D 217/24 | (2006.01) | |
| C07D 229/02 | (2006.01) | |
| C12N 15/113 | (2010.01) | |
| C12Q 1/68 | (2006.01) | |

(52) U.S. Cl.
CPC ............ *C12N 15/113* (2013.01); *C12Q 1/6876* (2013.01)
USPC ........... 544/287; 544/293; 544/314; 544/320; 544/332; 546/141; 546/143; 546/312; 548/960

(58) Field of Classification Search
USPC .......... 544/314, 332, 320, 293, 287; 546/312, 546/143, 141; 548/960
See application file for complete search history.

(56) References Cited

FOREIGN PATENT DOCUMENTS

| | | |
|---|---|---|
| EP | 1798225 A1 | 6/2007 |
| JP | 6479176 A | 3/1989 |
| JP | 0352889 A | 3/1991 |
| JP | 2005192484 A | 7/2005 |
| WO | 9614330 A1 | 5/1996 |
| WO | 2009113580 A1 | 9/2009 |
| WO | 2009120878 A2 | 10/2009 |
| WO | 2009129036 A1 | 10/2009 |
| WO | 2010091226 A1 | 8/2010 |

OTHER PUBLICATIONS

Notice of Reason(s) for Rejection 1; 2012-529033; Aug. 21, 2012.
Notice of Reason(s) for Rejection 2; 2012-529033; Nov. 7, 2012.
International Search Report; PCT/JP2011/077684; Feb. 21, 2012.
Ooi Takashi et al. (2999) "Remarkable catalytic activity of Me3Ga in the alkylation of hetero-substituted epoxides with alkynyl-lithiums" Tetrahedron Letters, vol. 40, No. 32, 5881-5884, 1999.
Malinovski et al. (1965) Zhurnal Obshchei Khimii. 36(6), 960-3.
Written Opinion of the International Searching Authority (English Translation); PCT/JP2011/077684; Jun. 4, 2013.
Extended European Search Report for EP Application No. 11844449.6, issued May 21, 2014.
Hui Zhou et al. (2009) "Pyrene acetylide nucleotides in GNA: probing duplex formation and sensing of copper(II) ions", Organic & Biomolecular Chemistry, vol. 7, No. 11, pp. 2297-2302.
Office Action for CN Application No. 201180057695.1, issued Jun. 17, 2014.

*Primary Examiner* — Kristin Vajda
(74) *Attorney, Agent, or Firm* — Westman, Champlin & Koehler, P.A.; Z. Peter Sawicki

(57) ABSTRACT

A nucleoside analog and a salt thereof represented by any of the general formulae (1) to (10) below:

(1)

(2)

(3)

(4)

-continued

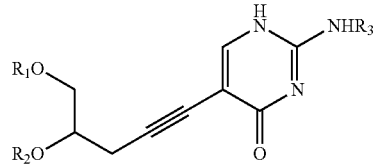
(5)

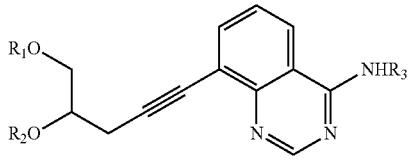
(6)

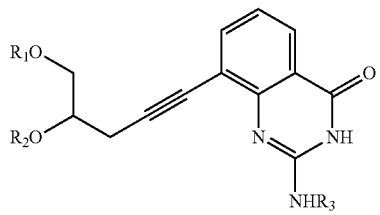
(7)

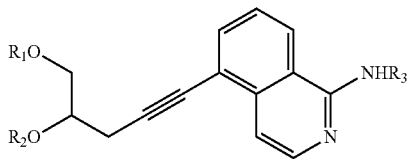
(8)

-continued

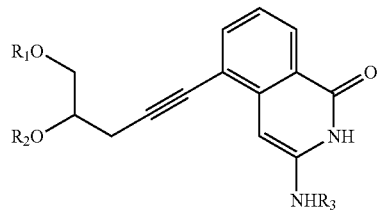
(9)

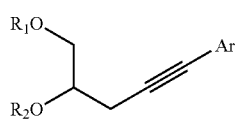
(10)

wherein $R_1$, $R_2$, and $R_3$ are the same or different groups, and each of the $R_1$, $R_2$ and $R_3$ is selected from a hydrogen atom, a protecting group for a functional group in nucleic acid synthesis, a phosphate group, a phosphate group protected by a protecting group in nucleic acid synthesis, and an activated phosphate group for solid phase synthesis; and Ar is one of an aromatic hydrocarbon group and a polyaromatic hydrocarbon group.

31 Claims, 11 Drawing Sheets

NUCLEOSIDE ANALOG OR SALT THEREOF, OLIGONUCLEOTIDE ANALOG, GENE EXPRESSION INHIBITOR, AND NUCLEIC-ACID PROBE FOR DETECTING GENE

CROSS-REFERENCE TO RELATED APPLICATIONS

This application is a 371 National Stage Application of International patent application Serial No. PCT/JP2011/077684, filed Nov. 30, 2011, and published as WO2012/074012A1, which claims priority based on Japanese Patent Application No. 2010-267314 filed Nov. 30, 2010 in the Japan Patent Office, and Japanese Patent Application No. 2011-190048 filed Aug. 31, 2011 in the Japan Patent Office, the entire contents of which are incorporated herein by reference.

TECHNICAL FIELD

The present invention relates to a nucleoside analog or a salt thereof, an oligonucleotide analog, a gene expression inhibitor, and a nucleic-acid probe for detecting gene.

BACKGROUND ART

A short double-stranded RNA, a microRNA (miRNA) and a small interfering RNA (siRNA) are an oligonucleotide containing a base sequence that is complementary to a target messenger RNA (mRNA). The target mRNA includes a base sequence of, for example, a gene responsible for a disease. RNA interference is defined as an in vivo gene inhibition mechanism in which a short double-stranded RNA, a miRNA and an siRNA inhibit expression of the gene of a target mRNA in vivo.

The siRNA is a double-stranded RNA which includes complementary base sequences. The siRNA combines with a target mRNA in a sequence specific manner. The siRNA combined with the target mRNA is incorporated into an RNA-induced silencing complex (RISC), so that the target mRNA is cut. If the base sequence of the gene responsible for a disease is apparent, it becomes possible to design and synthesize an siRNA which has a sequence complementary to the gene responsible for a disease. Therefore, the siRNA synthesized as described above can cut the gene responsible for a disease, and inhibit expression of a disease-related protein.

The miRNA is a double-stranded RNA which contains a partially mismatched base pair. The miRNA recognizes a target mRNA which partially has a complementary sequence, and combines with the target mRNA. When the miRNA combines with the target mRNA, the target mRNA is destabilized, thereby inhibiting translation of the target mRNA. As a result, expression of a gene is inhibited. It has been made clear that miRNA precisely control various biological functions such as generation, morphogenesis and cell growth of an organism. Recently, a pharmaceutical agent utilizing the RNA interference (a phenomenon of degrading an mRNA having a base sequence complementary to a double-stranded RNA) is actively studied. Especially, it is reported that the miRNA is associated with various diseases such as cancer.

For example, the expression amount of a let-7 miRNA is reduced in a lung cancer patient-derived cancer tissue. It has been reported that prognosis of a lung cancer patient can be determined by measuring the expression amount of the let-7 miRNA. Furthermore, it has been reported that the let-7 miRNA has proliferation-inhibiting effect on lung cancer (see Patent Document 1).

PRIOR ART DOCUMENTS

Patent Documents

Patent Document 1: Japanese Unexamined Patent Application Publication No. 2005-192484

SUMMARY OF THE INVENTION

Problems to be Solved by the Invention

However, the let-7 miRNA is a normal oligonucleotide. Therefore, the let-7 miRNA is readily degraded by a variety of nucleases present in bloods or cells. Thus, it was difficult to utilize the normal oligonucleotide such as a let-7 miRNA as a miRNA drug. A miRNA having increased nuclease resistance and improved gene expression-inhibiting effect compared to the miRNA formed with a normal oligonucleotide is desirable for development of a pharmaceutical drug utilizing the miRNA. However, as long as the inventor knows, a report regarding the above hardly exists.

Furthermore, the miRNA combines with the target mRNA in a state of partially containing a mismatched base pair. Therefore, a plurality of target mRNAs exist with respect to one miRNA. As a result, a human miRNA targets a tremendous number of mRNAs. Accordingly, it was difficult to determine the base sequence of a targeted mRNA. Since determination of the base sequence of a target mRNA leads to elucidation of the miRNA gene expression control mechanism, such a determination is one of the important problems to be studied in the life science field.

Under such a background, the present invention is intended to solve the above problems. An object of the present invention is to provide a nucleoside analog or a salt thereof and an oligonucleotide analog which have increased nuclease resistance and improved gene expression-inhibiting effect, and a nucleoside analog or a salt thereof and an oligonucleotide analog which can facilitate determination of the base sequence of a target mRNA.

Means for Solving the Problems

A characteristic structure employed in the present invention will be described below.

The nucleoside analog or the salt thereof according to the present invention is characterized by being the general formulae (1) to (10) (wherein $R_1$, $R_2$, and $R_3$ are the same or different groups, and each of the $R_1$, $R_2$, and $R_3$ is selected from a hydrogen atom, a protecting group for a functional group in nucleic acid synthesis, and a phosphate group; and Ar is one of an aromatic hydrocarbon group and a polyaromatic hydrocarbon group.)

[Chemical Formula 1]

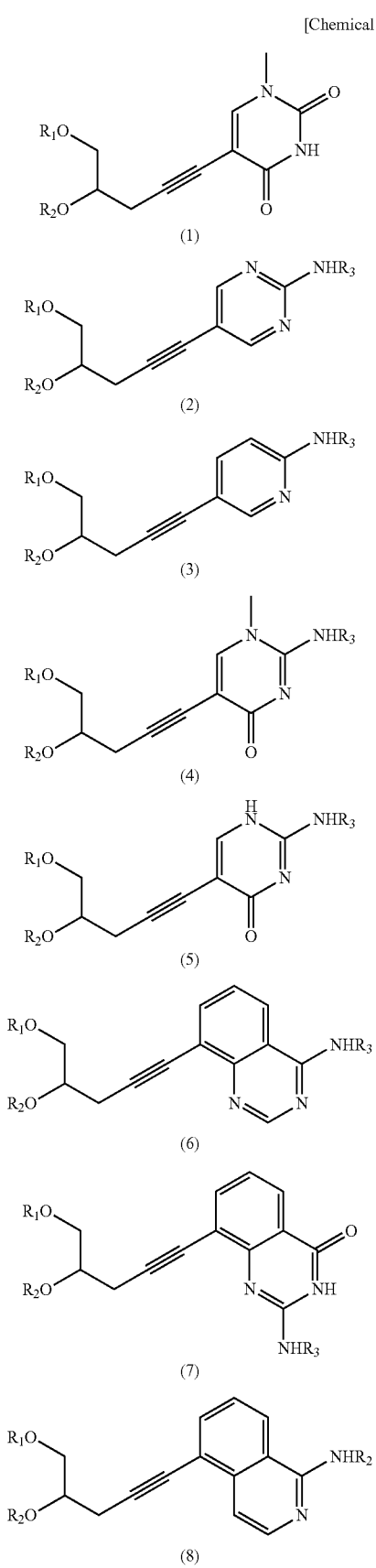
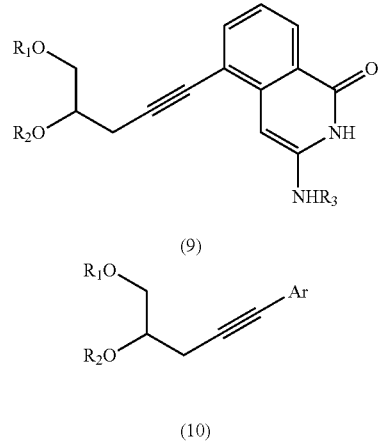

In the above general formulae (1) to (10), a portion corresponding to a sugar part of the nucleoside is ring opened, and includes a triple bond. Also, the above-described functional group includes a hydroxyl group and an amino group. The above-described protecting group is defined as an organic molecule which is introduced so as to protect a functional group such as a hydroxyl group and an amino group from proceeding with a side reaction.

The Ar in the general formula (10) is an aromatic hydrocarbon group or a polyaromatic hydrocarbon group, and is preferably a naphthalene group, an anthracene group, a phenanthrene group and a pyrene group.

In the above-described formulae (1) to (10), $R_1$ is preferably one of a hydrogen atom and a protecting group for a hydroxyl group that is a functional group in nucleic acid synthesis. $R_2$ is preferably selected from a hydrogen atom, a protecting group for a hydroxyl group that is a functional group in nucleic acid synthesis, and a phosphate group. $R_3$ is preferably a hydrogen atom or a protecting group for an amino group that is a functional group in nucleic acid synthesis.

Specific examples of the protecting group for a hydroxyl group that is a functional group in nucleic acid synthesis may include an aliphatic acyl group (e.g., an acetyl group), an aromatic acyl group (e.g., a benzoyl group), an alkyoxy group, a methyl group substituted with an aryl group (e.g., a benzyl group, a p-methoxybenzyl group, a 4,4'-dimethoxytrityl group, a 4-monomethoxytrityl group), a silyl group substituted with an aliphatic series (e.g., a tert-butyldimethylsilyl group), and a silyl group substituted with an aromatic series (e.g., a tert-butyldiphenylsilyl group).

Specific examples of the protecting group for an amino group that is a functional group in nucleic acid synthesis may include an aliphatic acyl group, an aromatic acyl group, an alkyoxy group, a methyl group substituted with an aryl group, a silyl group substituted with an aliphatic series, and a silyl group substituted with an aromatic series. Other than these, a sulfonyl group substituted with an aliphatic series, a sulfonyl group substituted with an aromatic series (e.g., a p-toluenesulfonyl group), a carbonyl group (e.g., a tert-butoxycarbonyl group, a benzyloxy carbonyl group), an amide group (a dimethylformamide group, a dimethylacetamide group) and the like may be included.

The phosphate group is preferably a phosphate group protected by a protecting group in nucleic acid synthesis, or an activated phosphate group for solid phase synthesis.

Specific examples of the phosphate group protected by a protecting group in nucleic acid synthesis may include a 2-chlorophenylphosphate group and a 4-chlorophenylphosphate group.

Specific examples of the activated phosphate group for solid phase synthesis may include —P(OC$_2$H$_4$CN)(N(CH(CH$_3$)$_2$)$_2$) and —P(OCH$_3$)(N(CH(CH$_3$)$_2$)$_2$).

The nucleoside analog or the salt thereof according to the present invention is characterized by being the general formula (11) below (wherein R$_1$ and R$_2$ are the same or different groups, and selected from a hydrogen atom, a protecting group for a hydroxyl group in nucleic acid synthesis, and a phosphate group; X$_1$ is a photoreactive group that reacts to light and provides active species capable of covalent bonding; and X$_2$ is an alkyl group or an alkyl group including at least one hydrogen substituted with halogen).

The photoreactive group in X$_1$ is defined as a group that absorbs light to generate a highly reactive intermediate carbene and can covalently bond with a target molecule.

Examples of the alkyl group in X$_2$ may include an alkyl group having 1 to 5 carbons. Examples of the halogen may include fluorine, chloride bromine and iodine.

[Chemical Formula 2]

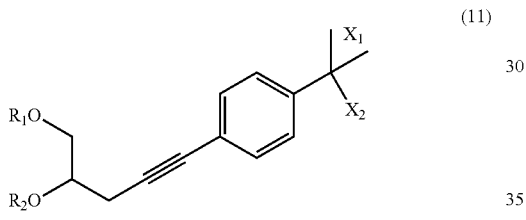

(11)

Furthermore, in the general formula (11), a portion corresponding to a sugar part of the nucleoside is ring-opened, and has a triple bond.

In the above general formula (11), R$_1$ and R$_2$ are preferably a group similar to the R$_1$ and R$_2$ described in the general formulae (1) to (10).

X$_1$ is preferably a diazirine group.

X$_2$ is preferably selected from a trifluoromethyl group, a difluoromethyl group and a monofluoromethyl group.

Also, the oligonucleotide analog according to the present invention is characterized by being an oligonucleotide analog which contains one or more structures represented by any of the formulae (1a) to (10a) as a component (wherein Ar is one of an aromatic hydrocarbon group and a polyaromatic hydrocarbon group).

[Chemical Formula 3]

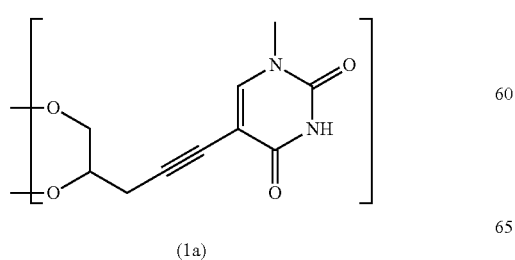

(1a)

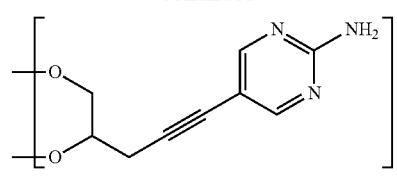

(2a)

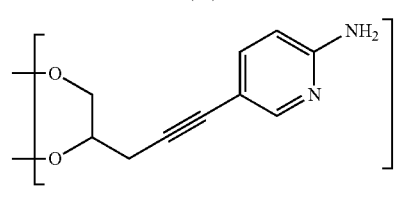

(3a)

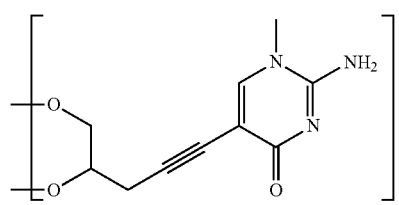

(4a)

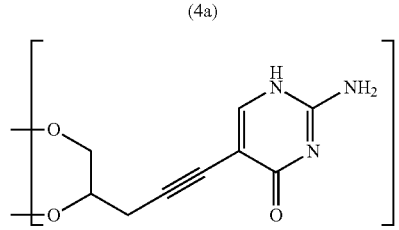

(5a)

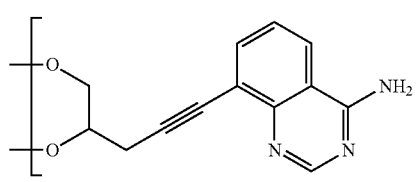

(6a)

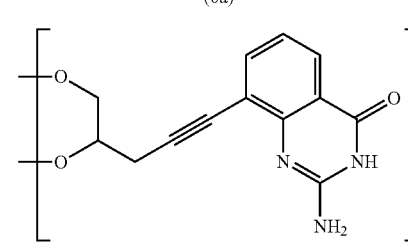

(7a)

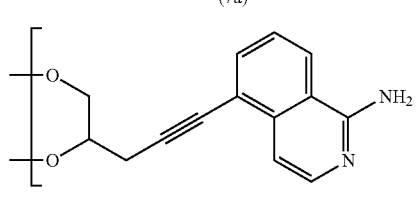

(8a)

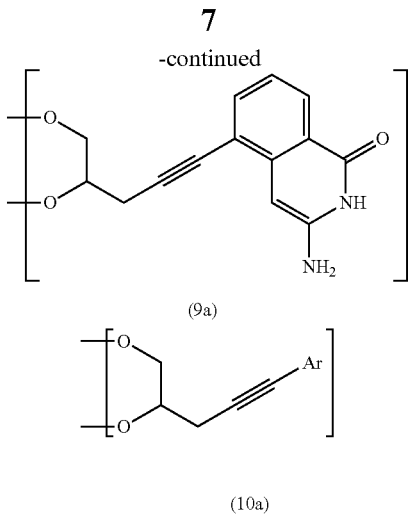

(9a)

(10a)

Also, the oligonucleotide analog according to the present invention is characterized by being an oligonucleotide analog which contains one or more structures represented by the formula (11a) as a component (wherein $X_1$ is a photoreactive group that reacts to light and provides active species capable of covalent bonding; and $X_2$ is an alkyl group or an alkyl group including at least one hydrogen substituted with halogen).

The photoreactive group in $X_1$ is defined as a group that absorbs light to generate a highly reactive intermediate carbene and can covalently bond with a target molecule.

Examples of the alkyl group in $X_2$ may include an alkyl group having 1 to 5 carbons. Examples of the halogen may include fluorine, chloride bromine and iodine.

[Chemical Formula 4]

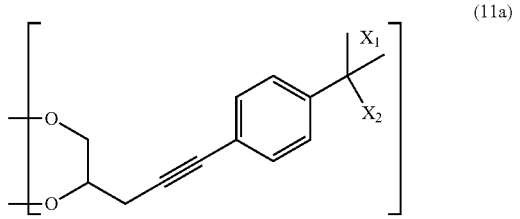

(11a)

In the above general formula (11a), $X_1$ is preferably a diazirine group.

$X_2$ is preferably selected from a trifluoromethyl group, a difluoromethyl group and a monofluoromethyl group.

Furthermore, in the above general formulae (1a) to (10a) and (11a), a portion corresponding to a sugar part of the nucleoside is ring-opened, and has a triple bond. An example of an oligonucleotide derivative forming the sugar-part ring-opened nucleoside is a glycol nucleic acid (GNA). The GNA has a structure in which a glycerol unit is repeated by a phosphoric diester bond. With respect to an (S)-GNA, it is known that the double strand of an (S)-GNA is stabilized due to the gauche effect. Thus, in the oligonucleotide analog that contains one or more of the similarly-structured formulae (1a) to (10a) and (11a) as a component, it is expected that the stability of a double strand is improved. Furthermore, since the formulae (1a) to (10a) and (11a) have an unsaturated bond, stacking interaction is formed between the oligonucleotides forming a double strand, thereby stabilizing the structure. Accordingly, loss in entropy when forming a double strand is reduced. As a result, it is expected that the double strand is thermodynamically stabilized.

"A salt thereof" according to the present invention is defined as a salt of the nucleoside analog and the oligonucleotide analog according to the present invention, since these analogs can be converted into a salt. Although the salt is not particularly limited, examples of the salt may suitably include alkali metal salts such as sodium salts, potassium salts and lithium salts, alkali earth metal salts such as calcium salts and magnesium salts, metal salts such as aluminum salts, iron salts, zinc salts, copper salts, nickel salts and cobalt salts, inorganic salts such as ammonium salts, amine salts as organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts and tris(hydroxymethyl)aminomethane salts, hydrohalic acid salts such as hydrofluoric acid salts, hydrochloric acid salts, hydrobromic acid salts and hydroiodic acid salts, inorganic acid salts such as nitric acid salts, perchloric acid salts, sulfuric acid salts and phosphoric acid salts, lower alkanesulfonic acid salts such as methane sulfonic acid salts, trifluoromethanesulfonic acid salts and ethanesulfonic acid salts, aryl sulfonic acid salts such as benzenesulfonic acid salts and p-toluenesulfonic acid salts, organic acid salts such as acetic acid salts, malic acid salts, fumaric acid salts, succinic acid salts, citric acid salts, tartaric acid salts, oxalic acid salts and maleic acid salts, and amino acid salts such as glycine salts, lysine salts, arginine salts, ornithine salts, glutamic acid salts and aspartic acid salts.

The oligonucleotide analog according to the present invention may be a single-stranded oligonucleotide or a double-stranded oligonucleotide. The single-stranded oligonucleotide may combine with an oligonucleotide which contains a sequence at least partially complementary to one strand to form a double strand. An oligonucleotide is defined as a polymer formed by polymerizing several to 100 nucleotides.

The gene expression inhibitor according to the present invention is characterized by containing the oligonucleotide analog according to the present invention.

The gene expression inhibitor is defined as a molecule which encourages a DNA or an mRNA to inhibit the process of replicating, transferring and translating a DNA or an mRNA.

The nucleic-acid probe for detecting gene according to the present invention is characterized by comprising an oligonucleotide analog which contains one or more structures represented by any of the above-described general formula (11a) as a component.

In the above general formula (11a), $X_1$ is preferably a diazirine group.

$X_2$ is preferably selected from a trifluoromethyl group, a difluoromethyl group and a monofluoromethyl group.

The nucleic-acid probe for detecting gene is defined as a short-stranded DNA or RNA molecule for visualizing and detecting a DNA or an mRNA.

Examples of such a nucleic-acid probe for detecting gene include a DNA microarray which comprises an oligonucleotide analog containing one or more structures represented by the formula (11a) as a component.

Effects of the Invention

According to the oligonucleotide analog containing one or more structures of the nucleoside analog according to the present invention (formulae (1) to (11)) as a component, the portions corresponding to the sugar part and the base part of a normal nucleoside are chemically modified, so that the oligonucleotide analog becomes difficult to be recognized by a nuclease. As a result, it is considered that nuclease resistance is increased compared to the normal oligonucleotide. Furthermore, it is considered that the gene expression-inhibiting effect can be increased compared to the normal oligonucleotide by the fact that thermodynamical stability of a miRNA is changed.

According to the gene expression inhibitor according to the present invention, the oligonucleotide analog containing one or more structures of the nucleoside analog according to the present invention (formulae (1) to (11)) as a component functions as a miRNA. The miRNA recognizes and combines with a target mRNA which has a partially complementary sequence, so that the target mRNA is destabilized, thereby inhibiting translation of the target mRNA. As a result, gene expression can be inhibited.

Furthermore, the oligonucleotide analog containing one or more structures of the oligonucleoside analog represented by the formula (11) as a component functions as a nucleic-acid probe for detecting gene. When the nucleic-acid probe for detecting gene is irradiated by light, active species capable of covalent bonding is formed. Therefore, the nucleic-acid probe for detecting gene is cross-linked with a target mRNA, thereby enabling capturing of the target mRNA. As a result, the base sequence of the captured mRNA can be determined by utilizing the nucleic-acid probe for detecting gene.

MODE FOR CARRYING OUT THE INVENTION

Figure 1:
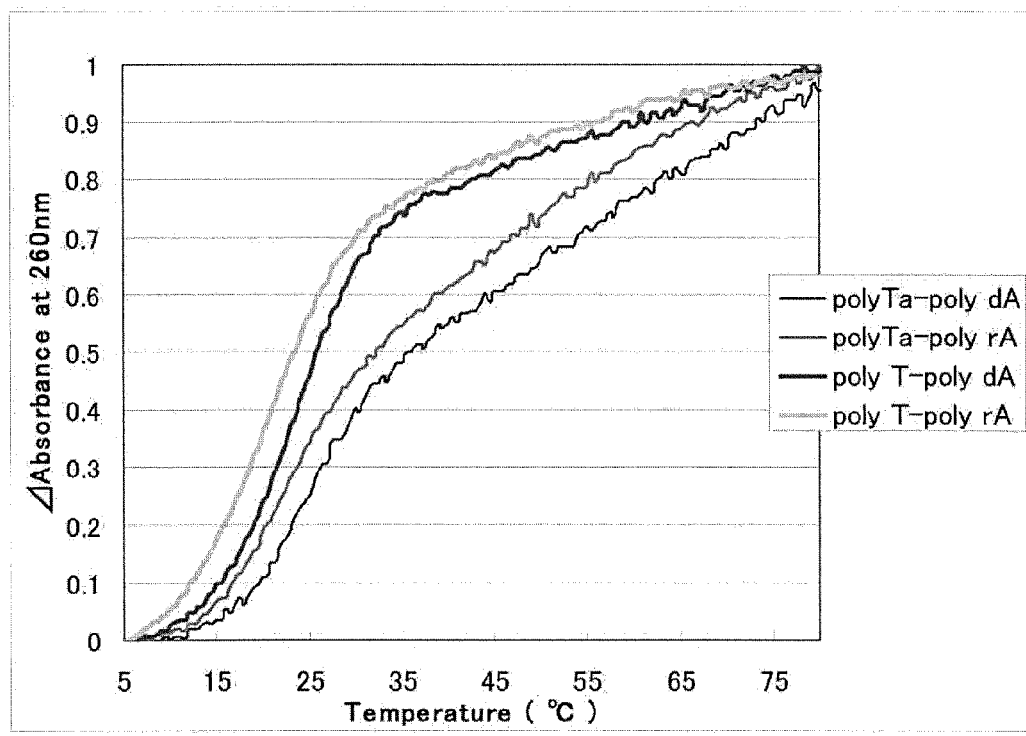
FIG. 1 is a graph illustrating results of Tm measurement.

Embodiments of the present invention will be described below.

Since abbreviations will be used herein, the list of abbreviations used herein will be first shown below.

LIST OF ABBREVIATIONS

BF$_3$EOEt: Boron trifluoride etherate THF: tetrahydrofuran
EtOAc: ethyl acetate
TBDMSCl: tert-Butyldimethylsilyl chloride
Pd(PPh$_3$): Tetrakis(triphenylphosphine)palladium
TEA: triethyamine
TBAF: Tetra-n-butylammonium fluoride
PdCl$_2$(PPh$_3$)$_2$: Bis(triphenylphosphine)palladium(II) chloride
TsCl: p-toluenesulfonyl chloride
DMAP: N,N-dimethyl-4-aminopyridine
DMTrCl: dimethoxytriphenylmethyl chloride
DIPEA: N,N-diisopropylethylamine
Amidite reagent, i-Pr$_2$NP(Cl)OCE: 2-cyanoethyldiisopropylchloro-phosphoramidite
DMF-DMA: N,N-Dimethylformamide dimethyl acetal
CPG: controlled-pore glass
WSC: water soluble carbidiimide
X-phos: 2-Dicyclohexylphosphino-2',4',6',-triisopropylbiphenyl
NaHCO$_3$ aq.: aqueous solution of sodium hydrogen carbonate
NaCl aq.: aqueous solution of sodium chloride
NMR: nuclear magnetic resonance
CDCl$_3$: Deuterochloroform
Tm: melting temperature

[Outline of Nucleoside Analog and Method of Synthesizing Nucleoside Analog]

Next, the outline of a nucleoside analog and a method of synthesizing the nucleoside analog will be described.

A sugar part of the nucleoside analog according to the present invention is synthesized by using as a starting material primary alcohol provided with an epoxy group. More particularly, first, after protecting a hydroxyl group of the primary alcohol provided with an epoxy group by a silyl compound, an acetylene group having a terminal protected with a silyl group is introduced when the epoxy group is ring-opened. Subsequently, a hydroxyl group formed by the ring-opening of an epoxy group is protected by the silyl group. Thereafter, the terminal silyl group of the acetylene side chain is selectively removed, thereby to obtain a sugar part precursor which enables a coupling reaction with a base part of the nucleoside analog according to the present invention described below.

On the other hand, the sugar part of the nucleoside analog according to the present invention is selected from a halogen substitution product in which one hydrogen atom of a heterocyclic ring is substituted with a halogen atom, a halogen substitution product in which one hydrogen atom of an aromatic hydrocarbon is substituted with a halogen atom, and a halogen substitution product in which one hydrogen atom of a polyaromatic hydrocarbon is substituted with a halogen atom. The halogen substitution product in which one hydrogen atom of an aromatic hydrocarbon is substituted with a halogen atom includes a halogen substitution product in which one hydrogen atom of the aromatic hydrocarbon, which has a photoreactive group that reacts to light and provides active species capable of covalent bonding as well as an alkyl group or an alkyl group having at least one hydrogen atom substituted with halogen, is substituted with a halogen atom.

The sugar part precursor and the base part described above are subjected to a coupling reaction in the presence of a palladium catalyst to obtain a coupling body. Thereafter, the silyl group is deprotected, and then processes of extraction, washing and purification are performed. Accordingly, a desired nucleoside analog can be obtained.

Next, an embodiment of the present invention will be described with reference to examples. However, the present invention is not limited to these examples. It is noted that, in the examples described below, to facilitate understanding of the relationship between the nucleoside analog exemplified as an example and the general formula explained earlier, the nucleoside analog described as an example of the nucleoside analog represented by a general formula (n) is designated as a nucleoside analog (n) (n is an integer of 1 to 11), utilizing the number (n) given to a general formula. However, this designation does not mean that the nucleoside analog represented by the general formula (n) is limited to the nucleoside analog (n) exemplified in the examples below.

EXAMPLES

1. Synthesis of nucleoside analog (1): (S)-5-(4,5-dihydroxypent-1-ynyl)-1-methylpyrimidine-2,4(1H,3H)-dione A nucleoside analog (1) was synthesized by means of Synthesis method 1 shown in [Chemical Formula 5] below.

[Chemical Formula 5]

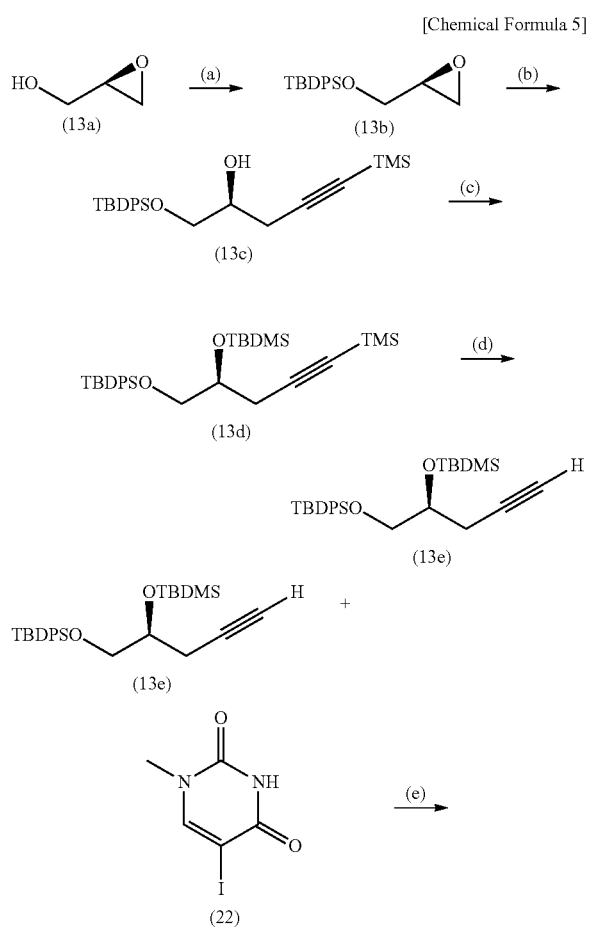

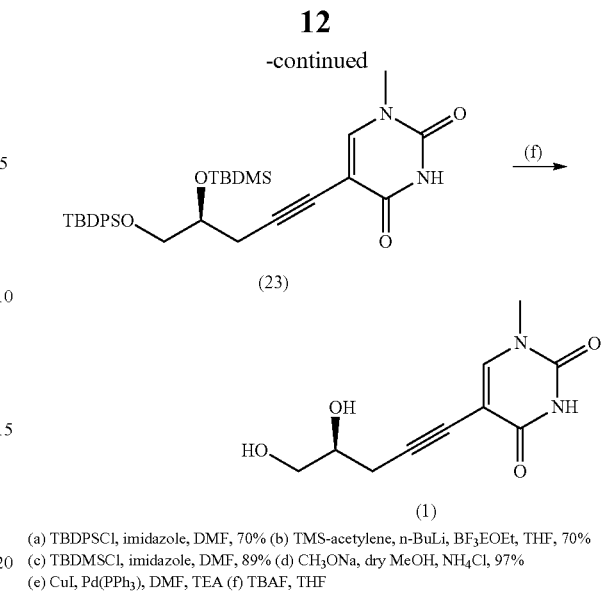

(a) TBDPSCl, imidazole, DMF, 70% (b) TMS-acetylene, n-BuLi, BF$_3$EOEt, THF, 70%
(c) TBDMSCl, imidazole, DMF, 89% (d) CH$_3$ONa, dry MeOH, NH$_4$Cl, 97%
(e) CuI, Pd(PPh$_3$), DMF, TEA (f) TBAF, THF <1.1. Synthetic Route (a) in Synthesis Method 1>

Imidazole (6.6 g, 97.2 mmol) and DMF (75 ml) were added to (R)-glycidol (2.7 ml, 40.5 mmol) (13a), and the resulting mixture was stirred. Then, TBDPSCl (12.6 ml, 48.6 mmol) was added and reacted at 0° C. overnight. Next day, after disappearance of the spots of the raw material was observed by thin-layer chromatography (TLC) (hereinafter referred to as TLC), the product was extracted with ethyl acetate and distilled water, to recover an organic layer. The organic layer was washed with saturated sodium hydrogen carbonate and a saturated salt solution, and dried with anhydrous sodium sulfate. The solvent was evaporated using a vacuum evaporator, and the residue was isolated and purified by silica gel column chromatography (hexane:ethyl acetate=50:1). Thus, a compound (13b) (S)-tert-butyl(oxiran-2-ylmethoxy)diphenylsilane (4.5664 g, 15 mmol, 37%) was obtained as a colorless and transparent liquid.

$^1$H NMR (400 MHz, CDCl$_3$) δ: 7.67-7.65 (4H, m), 7.41-7.35 (6H, m), 3.83 (1H, dd, J=12.0 Hz, 3.2 Hz), 3.69 (1H, dd, J=12.0 Hz, 4.8 Hz), 3.13-3.09 (1H, m), 2.73 (1H, dd, J=9.2 Hz, 4.0 Hz), 2.59 (1H, dd, J=5.2 Hz, 2.8 Hz), 1.0 (9H, s). $^{13}$C NMR (CDCl$_3$) δ: 135.5, 129.7, 127.7, 64.3, 52.2, 44.4, 26.7, 19.2.

<1.2. Synthetic Route (b) in Synthesis Method 1>

The compound (13b) (2.5268 g, 8.0 mmol) was added into a 50 ml pear-shaped flask under an argon atmosphere, and dissolved in THF (10 ml), to obtain a solution (A). TMS-acetylene (1.656 ml, 12.0 mmol), THF (10 ml), n-BuLi (7.2288 ml, 12.0 mmol) and BF$_3$.OEt$_2$ (1.5968 ml, 13.0 mmol) were added into a 50 ml recovery flask in this order under an argon atmosphere, and finally the solution (A) was added in the mixture. The obtained product was reacted at −78° C. overnight. Next day, after disappearance of the spots of the raw material was observed, NH$_4$Cl (20 ml) was added as a buffer to terminate the reaction. The reaction product was extracted with ethyl acetate and distilled water, to recover an organic layer. The organic layer was washed with saturated sodium hydrogen carbonate and a saturated salt solution, and dried with anhydrous sodium sulfate. The resulting product was decompressed and concentrated using a vacuum evaporator, and the residue was isolated and purified by silica gel column chromatography (hexane:ethyl acetate=20:1). Thus, a compound (13c): (S)-1-(tert-butyldiphenylsilyloxy)-5-(trimethylsilyl)pent-4-yn-2-ol) (2.2177 g, 5.4 mol, 67%) was obtained as a colorless and transparent liquid.

$^1$H NMR (400 MHz, CDCl$_3$) δ: 7.56-7.35 (4H, m), 7.34-7.18 (6H, m), 3.79-3.75 (1H, m), 3.62 (2H, ddd, J=25.6 Hz, 10.4 Hz, 4.4 Hz), 2.41-2.38 (2H, t, J=6.4 Hz), 0.96 (9H, s), 0.00 (9H, s). $^{13}$C NMR (CDCl$_3$) δ: 135.5, 129.8, 127.8, 102.7, 87.1, 70.2, 66.4, 44.4, 26.8, 19.3, 0.00

<1.3. Synthetic Route (c) in Synthesis Method 1>

Imidazole (1.103 g, 16.2 mmol), DMF (25 ml) and TBDM-SCl (1.238 g, 8.01 mmol) were added into a 50 ml pear-shaped flask under an argon atmosphere, and stirred. After stirring, the resulting solution was used as a solution (B). The compound (13c) (2.2177 g, 5.4 mmol) and DMF (25 ml) were added into a 50 ml recovery flask under an argon atmosphere, and stirred. Then the solution (B) was added, and the obtained mixture was reacted overnight. Next day, after disappearance of the spots of the raw material was observed, the product was extracted with ethyl acetate and distilled water, to recover an organic layer. The organic layer was washed with saturated sodium hydrogen carbonate and a saturated salt solution, and dried with anhydrous sodium sulfate. The resulting product was decompressed and concentrated using a vacuum evaporator, and the residue was isolated and purified by silica gel column chromatography (hexane:ethyl acetate=20:1). Thus, a compound (13d): (S)-2,2,3,3,9,9-hexamethyl-8,8-diphenyl-5-(3-(trimethylsilyl)prop-2-ynyl)-4,7-dioxa-3,8-disiladecane) (1.7713 g, 3.8 mmol, 62%) was obtained as a pale yellow liquid.

$^1$H NMR (400 MHz, CDCl$_3$) δ: 7.56-7.53 (4H, m), 7.31-7.22 (6H, m), 3.75-3.70 (1H, m), 3.51 (1H, dd, J=10.2 Hz, 4.6 Hz), 3.42 (1H, dd, J=10.4 Hz, 6.0 Hz), 2.54 (1H, dd, J=17.0 Hz, 5.4 Hz), 2.25 (1H, dd, J=17.0 Hz, 7.0 Hz), 0.96-0.88 (9H, m), 0.77-0.67 (9H, m), 0.047-0.00 (9H, m), −0.07 (3H, 5), −0.15 (3H, s). $^{13}$C NMR (CDCl$_3$) δ: 135.5, 129.5, 127.6, 104.7, 85.7, 71.8, 67.0, 26.7, 25.7, 19.2, 18.0, 0.00, −4.67.

<1.4. Synthetic Route (d) in Synthesis Method 1>

The compound (13d) (1.7713 g, 3.37 mmol) was dissolved in dry MeOH (35 ml) under an argon atmosphere, and reacted with CH$_3$ONa (2.37 ml, 4.39 mmol). After reacting at normal temperature for approximately 1 hour and then observing disappearance of the spots of the raw material by TLC, the product was extracted with ethyl acetate and distilled water, to recover an organic layer. The organic layer was washed with saturated sodium hydrogen carbonate and a saturated salt solution, and dried with anhydrous sodium sulfate. The resulting product was decompressed and concentrated using a vacuum evaporator, and a compound (13e): (S)-2,2,3,3,9,9-hexamethyl-8,8-diphenyl-5-(prop-2-ynyl)-4,7-dioxa-3,8-disiladecane) (1.4488 g, 3.2 mmol 95%) was obtained as a colorless and transparent liquid.

$^1$H NMR (400 MHz, CDCl$_3$) δ: 7.56-7.53 (4H, m), 7.29-7.23 (6H, m), 3.78-3.75 (1H, m), 3.52 (2H, ddd, J=21.2 Hz, 10.1 Hz, 5.5 Hz), 2.52 (1H, ddd, J=16.8 Hz, 5.5 Hz, 2.8 Hz), 2.29 (1H, ddd, J=16.7 Hz, 6.2 Hz, 2.7 Hz), 1.86 (1H, t, J=2.7 Hz), 0.98 (9H, 5), 0.79 (9H, s), 0.00 (3H, s), −0.08 (3H, s). $^{13}$C NMR (CDCl$_3$) δ: 135.5, 129.7, 127.8, 81.8, 71.7, 69.7, 66.9, 26.8, 25.8, 24.4, 19.3, 18.1, −4.72.

<1.5. Synthetic Route (e) in Synthesis Method 1>

A compound (22) (0.70 g, 2.78 mmol) and the compound (13e) (1.93 g, 1.2 eq.) were dissolved in DMF (27.8 ml). Pd(PPh$_3$)$_4$ (0.16 g, 0.05 eq.) and CuI (0.053 g, 0.1 eq.) were added and stirred, and then TEA (0.97 ml, 2.5 eq.) was added. The mixture was reacted at 40° C. After stirring overnight, the reaction solution was celite-filtered with EtOAc. After filtering, the filtrate was extracted with EtOAc and H$_2$O to recover an organic layer. The organic layer was washed with NaHCO$_3$ aq. and NaCl aq., and concentrated using a vacuum evaporator. The residue was isolated and purified by silica gel column chromatography (using neutral silica, elution solvent: CHCl$_3$:CH$_3$OH=100:1). Thus, a coupling body (23): (S)-5-(4-(tert-butyldimethylsilyloxy)-5-(tert-butyldiphenylsilyloxy)pent-1-ynyl)-1-methylpyrimidine-2,4(1H, 3H)-dione) (yield: 1.62 g) was obtained.

$^1$H NMR (CDCl$_3$) δ: 8.68 (1H, s) 7.95 (1H, s) 7.63-7.10 (10H, m) 3.88-3.86 (3H, t, J=5.96, 5.04) 3.63-3.59 (1H, dd, J=5.04, 5.04) 3.56-3.52 (1H, dd, J=5.96, 5.96) 3.27 (3H, s) 2.78-2.72 (1H, dd, J=5.96, 5.52) 2.55-2.49 (1H, dd, J=6.44, 6.44) 0.98 (9H, s) 0.80 (9H, s) −0.00 (3H, s) −0.07 (3H, s) $^{13}$C NMR (CDCl$_3$): 161.8, 149.9, 146.8, 135.6, 132.0, 127.6, 100.5, 92.6, 71.7, 67.1, 64.3, 36.1, 31.4, 26.8, 25.7, 19.2, 18.0, −4.65

<1.6. Synthetic Route (f) in Synthesis Method 1>

The coupling body (23) (1.62 g, 2.78 mmol) was dissolved in THF (11.2 ml), and then 1 mol/l TBAF (5.88 ml, 2.1 eq.) was added and stirred overnight. TLC was used to confirm termination of the reaction, and the resulting product was decompressed and concentrated. Thereafter, the residue was isolated and purified by silica gel column chromatography (neutral silica, CHCl$_3$ only to CHCl$_3$:MeOH=15:1). Thus, a nucleoside analog (1) (yield: 0.33 g, 52.2%) was obtained.

$^1$H NMR (DMSO) δ: 7.94 (1H, s) 4.84-4.82 (1H, d, J=4.88) 4.60-4.57 (1H, t, J=5.84-5.60) 3.60-3.56 (1H, dd, J=5.84, 5.60) 3.39-3.35 (1H, dd) 3.31 (1H, s) 3.17-3.13 (1H, dd) 2.54-2.50 (1H, dd) 2.40-2.35 (1H, dd)

Example 2

2. Synthesis of nucleoside analog (3): (S)-5-(6-aminopyridin-3-yl)pent-4-yne-1,2-diol)

A nucleoside analog (3) was synthesized by means of Synthesis method 2 shown in [Chemical Formula 6]below.

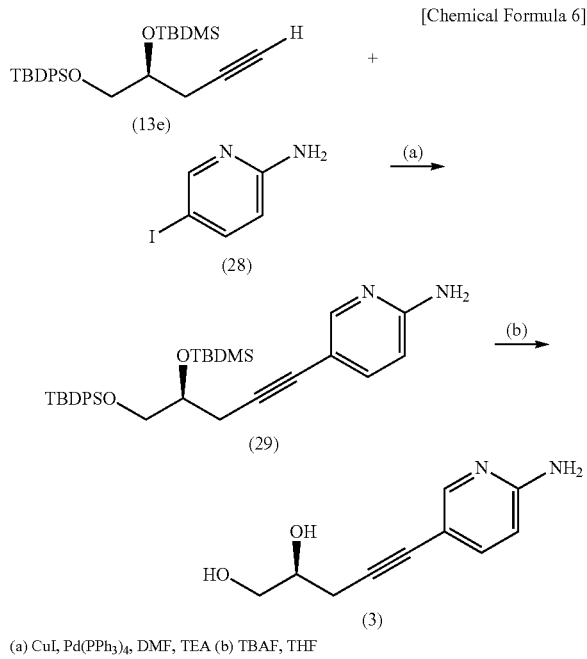

[Chemical Formula 6]

(a) CuI, Pd(PPh$_3$)$_4$, DMF, TEA (b) TBAF, THF

<2.1. Synthetic Route (a) in Synthesis Method 2>

A sugar part (13e) (0.76 g, 3.45 mmol) and a base part (28) (1.87 g, 1.3 eq.) were added into a flask, and dissolved in DMF (35.0 ml). Pd(PPh₃)₄ (0.40 g, 0.1 eq.) and CuI (0.13 g, 0.2 eq.) were added and stirred, and then TEA (1.20 ml, 2.5 eq.) was added to perform a reaction at 45° C. After stirring overnight, the reaction solution was celite-filtered with EtOAc. After filtering, the filtrate was extracted with EtOAc and H₂O to recover an organic layer. The organic layer was washed with NaHCO₃ aq. and NaCl aq., and concentrated using a vacuum evaporator. The residue was isolated and purified by silica gel column chromatography (using neutral silica, and CHCl₃ as elution solvent). Thus, a coupling body (29): (S)-5-(4-(tert-butyldimethylsilyloxy)-5-(tert-butyldiphenylsilyloxy)pent-1-ynyl)pyridin-2-amine) (yield: 1.35 g, 71.5%) was obtained.

<2.2. Synthetic Route (b) in Synthesis Method 2>

The coupling body (29) (1.0 g, 1.73 mmol) was dissolved in THF (17.3 ml), and then 1 mol/l TBAF (3.6 ml, 2.1 eq.) was added. The mixture was stirred overnight. Thereafter, the solvent was removed, and the residue was isolated and purified by silica gel column chromatography (using neutral silica, elution solvent: CHCl₃:MeOH=1:0 and above). Thus, a nucleoside analog (3) (yield: 0.47 g) was obtained.

Example 3

3. Synthesis of nucleoside analog (5): (S)-2-amino-5-(4,5-dihydroxypent-1-ynyl)pyrimidin-4(1H)-one A nucleoside analog (5) was synthesized by means of Synthesis method 3 shown in [Chemical Formula 7] below.

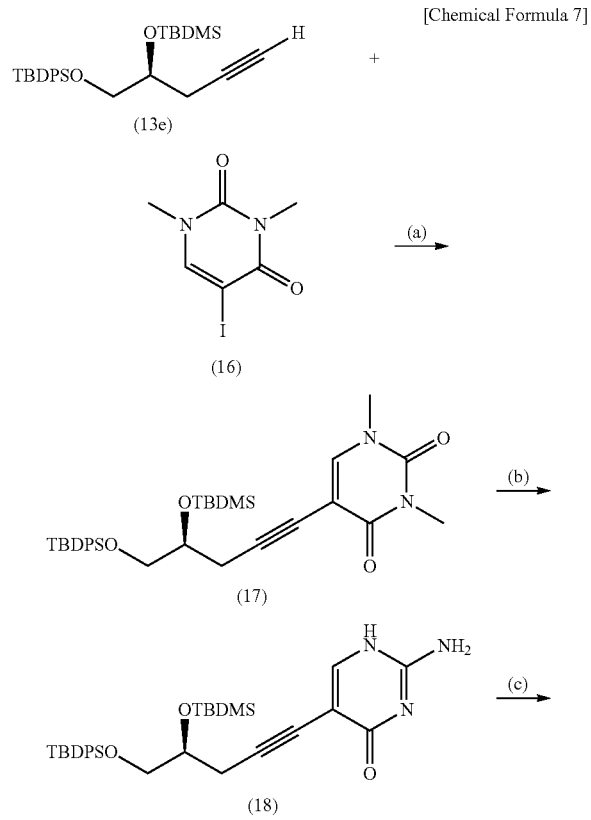

[Chemical Formula 7]

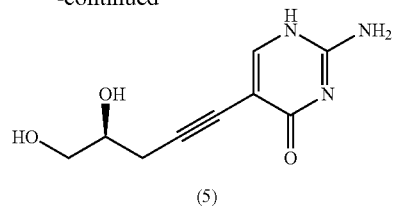

(a) CuI, PdCl₂(PPh₃)₂, DMF, TEA, 51%
(b) CH₃CH₂ONa, guanidine hydrochloride, dry EtOH, 56%, 100 eq. 70 eq.
(c) 12N HCl, dry MeOH <3.1. Synthetic Route (a) in Synthesis Method 3>

A compound (16): 5-iodo-1,3-dimethyluracil (0.5 g, 1.88 mmol), PdCl₂(PPh₃)₂ (10.99 mg, 0.01566 mmol), CuI (5.965 mg, 0.03132 mmol), the compound (13e) (0.71 g, 1.566 mmol) and DMF (10 ml) were added into a flask in this order and stirred for 17 hours. After confirming completion of the reaction, the reaction product was extracted with ethyl acetate and distilled water, to recover an organic layer. The organic layer was washed with saturated sodium hydrogen carbonate and a saturated salt solution, and dried with anhydrous sodium sulfate. The organic layer was decompressed and concentrated using a vacuum evaporator. The residue was isolated and purified by silica gel column chromatography (elution solvent: chloroform:methanol=100:1). Thus, a compound (17): (S)-5-(4-(tert-butyldimethylsilyloxy)-5-(tert-butyldiphenylsilyloxy)pent-1-ynyl)-1,3-dimethylpyrimidine-2,4(1H,3H)-dione (yield: 0.4715 g, 0.8 mmol, 51%, yellow liquid) was obtained.

¹H NMR (400 MHz, CDCl₃) δ: 7.70-7.63 (4H, m), 7.40-7.37 (6H, m), 3.96-3.90 (1H, m), 3.69-3.66 (1H, dd, J=10.4 Hz, 4.8 Hz), 3.63-3.59 (1H, dd, J=10.4 Hz, 4.8 Hz), 3.37 (6H, s), 2.85-2.79 (1H, dd, J=13.8 Hz, 6.00 Hz), 2.60-2.55 (1H, dd, J=13.8 Hz, 6.00 Hz), 1.04 (9H, s), 0.83 (9H, s), 0.06 (3H, s), 0.00 (3H, s)

<3.2. Synthetic Route (b) in Synthesis Method 3>

Guanidine hydrochloride (24.8 g, 0.2596 mol) and sodium ethoxide (12.37 g, 0.182 mol) were dissolved in dry ethanol (100 ml), and stirred for 40 minutes. Then the resulting mixture was celite-filtered. The filtrate was decompressed and concentrated using a vacuum evaporator. The obtained oil was transferred into a two-diameter recovery flask. A Dimroth was attached to the two-diameter recovery flask. Into the two-diameter recovery flask, the compound 17 (1.534 g, 2.60 mmol) dissolved in dry ethanol (100 ml) was added, and stirred for 1.5 hours while the temperature was maintained at 96° C. After the reaction was completed, the reaction solution was decompressed and concentrated using a vacuum evaporator. The obtained residue was isolated and purified by silica gel column chromatography (chloroform:methanol=100:1). Thus, a compound (18): (S)-2-amino-5-(4-(tert-butyldimethylsilyloxy)-5-(tert-butyldiphenylsilyloxy)pent-1-ynyl)pyrimidin-4(1H)-one) (0.813 g, 1.45 mmol, 56%, yellow liquid) was obtained.

<3.3. Synthetic Route (c) in Synthesis Method 3>

The compound (18) (0.793 g, 1.41 mmol) was dissolved in dry MeOH (40 ml) under an argon atmosphere, and then 12 mol/l HCl (0.353 ml, 4.23 mmol) was added. The obtained mixture was stirred for 4 hours while the temperature was maintained at 60° C. in an oil bath. After the reaction, the reaction product was decompressed and concentrated using a vacuum evaporator to obtain a nucleoside analog (5). The nucleoside analog (5) was proceeded to the next reaction without post-treatment.

Example 4

4. Synthesis of nucleoside analog (10): (S)-5-(anthracen-9-yl)pent-4-yne-1,2-diol A nucleoside analog (10) was synthesized by means of Synthesis method 4 shown in [Chemical Formula 8] below.

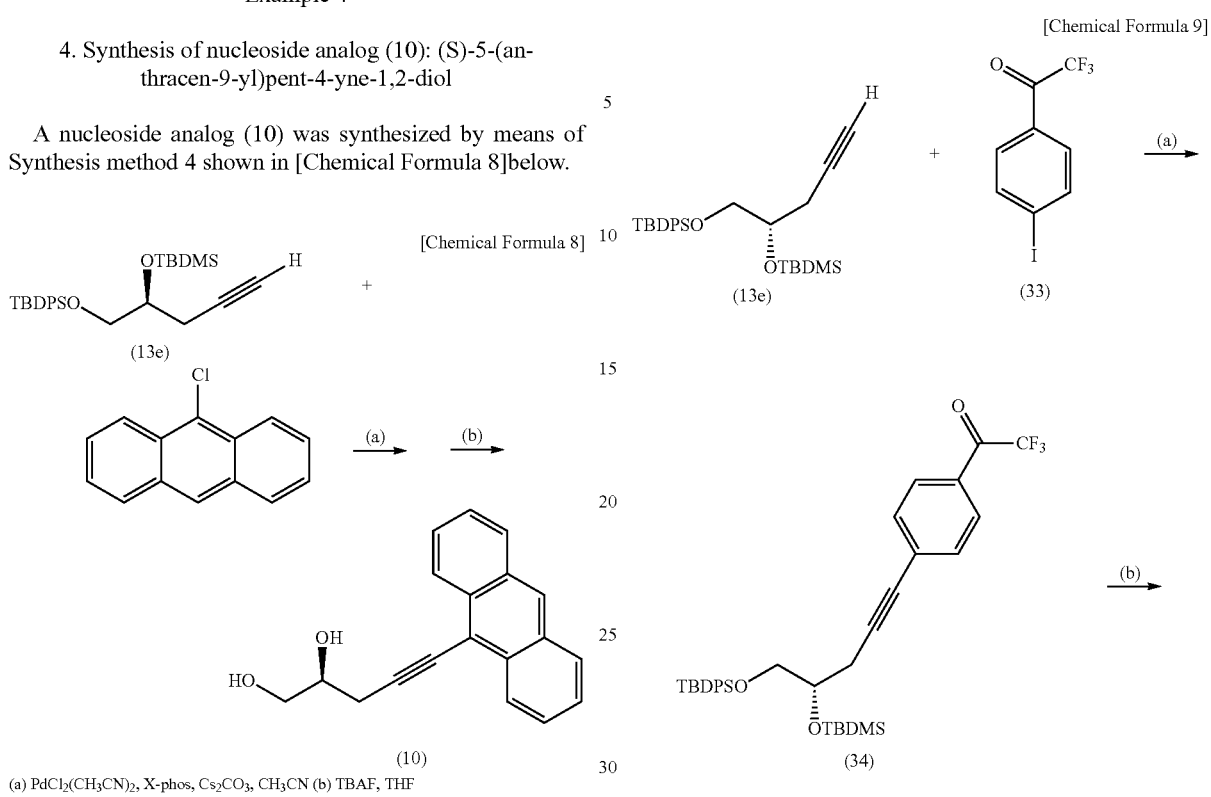

(a) PdCl$_2$(CH$_3$CN)$_2$, X-phos, Cs$_2$CO$_3$, CH$_3$CN (b) TBAF, THF

<4.1. Synthetic Routes (a) and (b) in Synthesis Method 4>

Into a flask in which the compound (13e) (0.86 g, 1.89 mmol) was poured, PdCl$_2$(CH$_3$CN)$_2$ (19.6 mg, 75.6 μmol), X-Phos (108 mg, 227 μmol), Cs$_2$CO$_3$ (1.60 g, 4.92 mmol), and 9-chloro anthracene (1.21 g, 5.6 mmol) were put in this order, and then acetonitrile (15 ml) was added for dissolution. The resulting mixture was reacted at 90° C. After reacting overnight, the reaction product was extracted with ethyl acetate and H$_2$O. An aqueous layer was collected, and extracted with ethyl acetate and H$_2$O again. An organic layer was collected, and dried with anhydrous sodium sulfate. The solvent was decompressed and distilled away. (b) The obtained residue was dissolved in THF (15 ml), and TBAF (7.1 ml, 7.11 mmol) was poured and stirred. After the reaction was completed, the solvent was decompressed and distilled away. The residue was purified by silica gel column chromatography (hexane:ethyl acetate=1:1), and the eluate was decompressed and distilled away. Thus, a nucleoside analog (10) (yield: 0.14 g, 26%, brown solid) was obtained.

$^1$H NMR (400 MHz, CHCl$_3$) δ: 1.97-2.00 (m, 1H, C1-Hα), 2.52-2.53 (m, 1H, C1-Hβ), 3.02-3.04 (m, 2H, OH), 3.81-3.85 (dd, 1H, C3-Hα, J=5.52, 11.5 Hz), 3.95-3.99 (dd, 1H, C3-Hβ, J=5.68, 11.5 Hz), 4.14-4.20 (m, 1H, C2-H), 7.25-7.28 (m, 2H, anthracene), 7.49-7.56 (m, 3H, anthracene), 7.99-8.01 (m, 2H, anthracene), 8.41-8.51 (m, 2H, anthracene)

Example 5

5. Synthesis of nucleoside analog (11): (S)-5-(4-(3-(trifluoromethyl)-3H-diazirin-3-yl)phenyl)pent-4-yne-1,2-diol A nucleoside analog (11) was synthesized by means of Synthesis method 5 shown in [Chemical Formula 9] below.

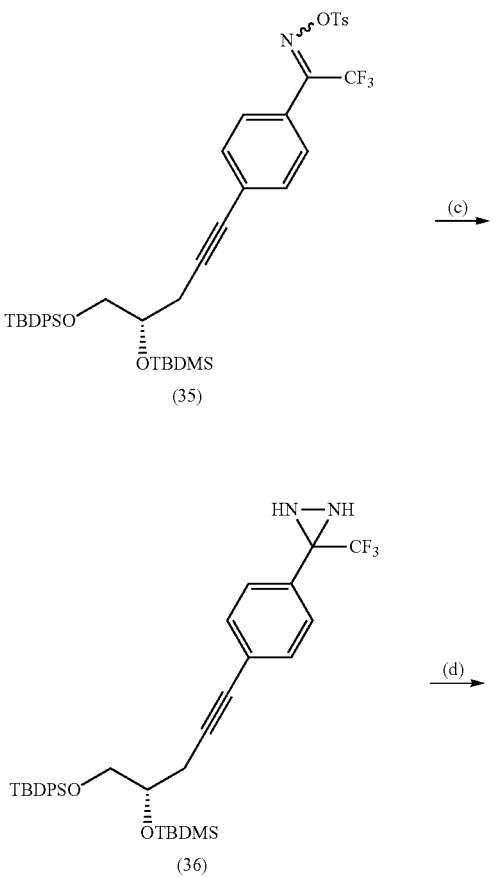

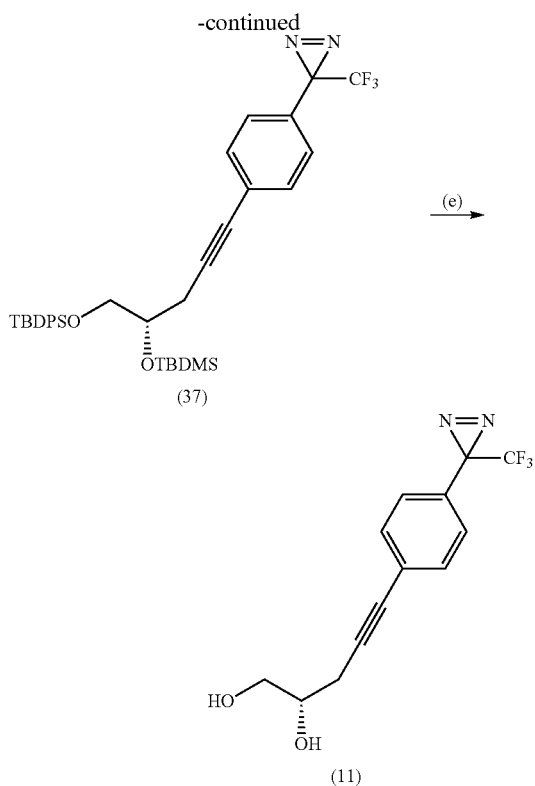

(37)

(11)

(a) CuI, PdCl$_2$(PPh$_3$)$_2$, DMF, TEA, 50%
(b) 1. HONH$_2$·HCl, EtOH, pyridine, 2. TsCl, TEA, DMAP, CH$_2$Cl$_2$, 48%
(c) NH$_3$ gas, THF, 80% (d) I$_2$, TEA, MeOH, 93% (e) TBAF, THF, 94%

<5.1. Synthetic Route (a) in Synthesis Method 5>

Under an argon atmosphere, a sufficiently dried compound (33): 4'-iodo-2,2,2-trifluoroacetophenone (0.18 g, 0.60 mmol) was poured into a flask. Then, PdCl$_2$(PPh$_3$)$_2$ (0.017 g, 0.024 mmol, 0.04 eq.) and CuI (0.009 g, 0.048 mmol, 0.08 eq.) were added, and dissolved in DMF (3 ml). Into this flask, a sufficiently dried compound (13e) (0.30 g, 0.66 mmol, 1.1 eq.) dissolved in DMF (3 ml) and TEA (0.25 ml, 1.8 mmol, 3.0 eq.) were added, and stirred at 80° C. to initiate reaction. After stirring overnight and then confirming completion of the reaction, the reaction solution was celite-filtered to decompress and remove the volatile substances. The obtained residue was extracted with ethyl acetate and H$_2$O. The organic layer was washed with saturated sodium hydrogen carbonate and a saturated salt solution, and dried with anhydrous sodium sulfate. The solvent was decompressed and distilled away. The residue was purified by silica gel column chromatography (hexane:ethyl acetate=100:1). Thus, a compound (34): (S)-1-(4-(4-(tert-butyldimethylsilyloxy)-5-(tert-butyldiphenylsilyloxy)pent-1-ynyl)phenyl)-2,2,2-trifluoroethanone) (0.19 g, 0.29 mmol, 50%, brown oil form) was obtained.

$^1$H NMR (400 MHz, CDCl$_3$) δ: −0.074 (s, 3H, -TBDMS), −0.012 (s, 3H, -TBDMS), 0.79 (s, 9H, -TBDMS), 0.97 (s, 9H, -TBDPS), 2.42-2.48 (q, J=10.4 Hz, 1H), 2.69-2.75 (q, J=12.2 Hz, 1H), 3.56-3.62 (m, 1H), 3.64-3.85 (m, 2H), 7.25-7.64 (m, 10H, -TBDPS), 7.61-7.62 (d, 2H), 7.91-7.93 (d, 2H). $^{19}$F NMR (372 MHz, CDCl$_3$) δ: −87.4 (s, 3F, —CF$_3$).

<5.2. Synthetic Route (b) in Synthesis Method 5>

Under an argon atmosphere, the compound (34) (0.19 g, 0.2 mmol) and HONH$_2$·HCl (0.040 g, 0.58 mmol, 2.0 eq.) were added into a flask, and dissolved in dry EtOH (3 ml) and dry pyridine (3 ml). The resulting mixture was stirred at 60° C. to initiate a reaction. After reacting overnight, the reaction product was extracted with chloromethane and distilled water. The organic layer was washed with saturated sodium hydrogen carbonate and a saturated salt solution, and dried with anhydrous sodium sulfate to decompress and distill away the solvent. The obtained residue was dissolved in an appropriate amount of CH$_2$Cl$_2$. Into the flask, TEA (0.24 ml, 1.7 mmol, 4.0 eq.) and TsCl (0.083 g, 0.44 mmol, 1.5 eq.) were added. Then, DMAP as a catalyst was added in a small amount to initiate reaction at room temperature. After reacting overnight, volatile substances were decompressed and removed, and the obtained residue was extracted with chloroform and H$_2$O. The organic layer was washed with saturated sodium hydrogen carbonate and a saturated salt solution, and dried with anhydrous sodium sulfate. The solvent was decompressed and distilled away. The residue was purified by silica gel column chromatography (hexane:ethyl acetate=100:1). Thus, a compound (35): (S)-1-(4-(4-(tert-butyldimethylsilyloxy)-5-(tert-butyldiphenylsilyloxy)pent-1-ynyl)phenyl)-2,2,2-trifluoroethanone O-tosyl oxime) (0.11 g, 0.13 mmol, 48%, white solid) was obtained.

$^1$H NMR (400 MHz, CDCl$_3$) δ: −0.074 (s, 3H, -TBDMS), −0.012 (s, 3H, -TBDMS), 0.79 (s, 9H, -TBDMS), 0.97 (s, 9H, -TBDPS), 2.42-2.48 (q, J=10.4 Hz, 1H), 2.47-2.49 (d, 3H, -Ts), 2.69-2.75 (q, J=12.2 Hz, 1H), 3.56-3.62 (m, 1H), 3.64-3.85 (m, 2H), 7.25-7.64 (m, 10H, -TBDPS), 7.40-7.69 (m, 4H, -Ts), 7.61-7.62 (d, 2H), 7.91-7.93 (d, 2H). $^{19}$F NMR (372 MHz, CDCl$_3$) δ: −91.5 (s, 3F, —CF$_3$).

<5.3. Synthetic Route (c) in Synthesis Method 5>

Under an argon atmosphere, a sealed tube was cooled to −78° C. Thereafter, the compound (34) (0.11 g, 0.13 mmol) was poured into the sealed tube. Then, THF (4 ml) was added for dissolution. An appropriate amount of NH$_3$ gas was blown into the solution, the tube was sealed, and stirring was performed at normal temperature for 2 days. After cooling to −78° C., the tube was opened, and returned to normal temperature so as to volatilize excess NH$_3$ gas. The volatile solvent was decompressed and concentrated using a vacuum evaporator. The residue was purified by silica gel column chromatography (hexane:ethyl acetate=9:1). Thus, a compound (36): (S)-3-(4-(4-(tert-butyldimethylsilyloxy)-5-(tert-butyldiphenylsilyloxy)pent-1-ynyl)phenyl)-3-(trifluoromethyl)diaziridine (0.79 g, 2.95 mmol, 80%, brown oil) was obtained.

$^1$H NMR (400 MHz, CDCl$_3$) δ: −0.074 (s, 3H, -TBDMS), −0.012 (s, 3H, -TBDMS), 0.79 (s, 9H, -TBDMS), 0.97 (s, 9H, -TBDPS), 2.42-2.48 (q, J=10.4 Hz, 1H), 2.12-2.74 (m, 2H, —NH—NH—), 2.69-2.75 (q, J=12.2 Hz, 1H), 3.56-3.62 (m, 1H), 3.64-3.85 (m, 2H), 7.25-7.64 (m, 10H, -TBDPS), 7.61-7.62 (d, 2H), 7.91-7.93 (d, 2H). $^{19}$F NMR (372 MHz, CDCl$_3$) δ: −91.2 (s, 3F, -CFO.

<5.4. Synthetic Route (d) in Synthesis Method 5>

The compound (36) (0.51 g, 0.80 mmol) was dissolved in dry MeOH (16 ml) under an argon atmosphere. Under a light shielding condition, TEA (0.30 ml, 2.0 mmol, 2.5 eq.) and I$_2$ (0.22 g, 0.88 mmol, 1.1 eq.) were added, to initiate reaction. After 30 minutes, disappearance of the raw material was confirmed. Then, the reaction product was extracted with diethyl ether and sodium thiosulfate. An organic layer was recovered, washed with saturated sodium hydrogen carbonate and a saturated salt solution, and dried with anhydrous sodium sulfate. The solvent was decompressed and distilled away. The residue was purified by silica gel column chromatography (hexane:ethyl acetate=40:1). Thus, a compound (37): (S)-3-(4-(4-(tert-butyldimethylsilyloxy)-5-(tert-butyldiphenylsilyloxy)pent-1-ynyl)phenyl)-3-(trifluoromethyl)-3H-diazirine) (0.48 g, 0.75 mmol, 93%, colorless crystal) was obtained.

$^1$H NMR (400 MHz, CDCl$_3$) δ: −0.073 (s, 3H, -TBDMS), 0.00 (s, 3H, -TBDMS), 0.79 (s, 9H, -TBDMS), 0.99 (s, 9H, -TBDPS), 2.49-2.55 (q, 1H), 2.75-2.80 (q, 1H), 3.53-3.64 (m, 1H), 3.86-4.03 (m, 2H), 7.01-7.04 (d, 2H), 7.19-7.37 (m, 10H, -TBDPS), 7.60-7.63 (d, 2H). $^{19}$F NMR (372 MHz, CDCl$_3$) δ: −80.9 (s, 3F, —CF$_3$).

<5.5. Synthetic Route (e) in Synthesis Method 5>

Under an argon atmosphere, the compound (37) (0.44 g, 0.68 mmol) was added into a flask, and THF (13.6 ml) was added for dissolution. Then, 1.0 mol/l TBAF (1.42 ml, 1.42 mmol, 2.1 eq.) was added to initiate reaction at room temperature. After 2 hours, disappearance of the raw material was confirmed. Then the solvent was decompressed and distilled away. The obtained residue was purified by silica gel column chromatography (chloroform:methanol=50:1). Thus, a nucleoside analog (11) (0.18 g, 0.64 mmol, 94%, colorless crystal) was obtained.

$^1$H NMR (400 MHz, CDCl$_3$) δ: 2.65-2.67 (m, 2H, —OH), 3.63-3.67 (q, 2H), 3.78-3.81 (q, 1H), 3.95-3.97 (m, 2H), 7.08-7.10 (d, 2H), 7.38-7.41 (d, 2H). $^{19}$F NMR (372 MHz, CDCl$_3$) δ: −80.9 (s, 3F, —CF$_3$).

Example 6

6. Synthesis of amidite body (25) of nucleoside analog (1): (S)-1-(bis(4-methoxyphenyl)(phenyl)methoxy)-5-(1-methyl-2,4-dioxo-1,2,3,4-tetrahydropyrimidin-5-yl)pent-4-yn-2-yl 2-cyanoethyl diisopropylphosphoramidite An amidite body (25) was synthesized by means of Synthesis method 6 shown in [Chemical Formula 10] below.

[Chemical Formula 10]

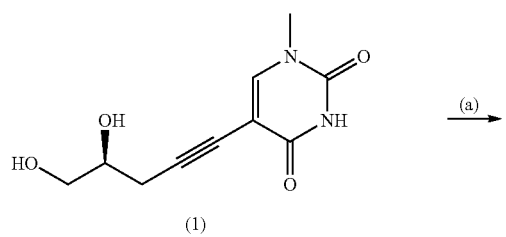

(1)

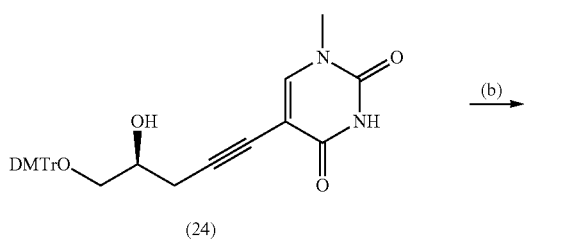

(24)

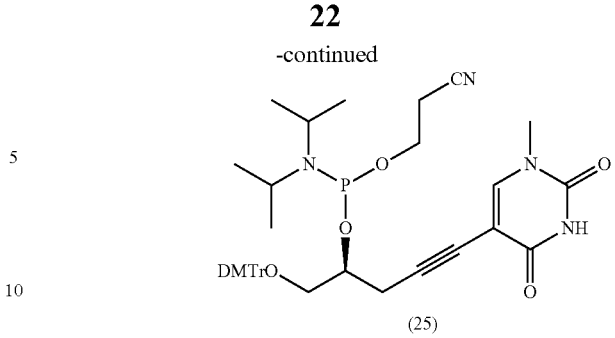

(25)

(a) DMTrCl, dry pyridine (b) DIPEA, amidite, THF

<6.1. Synthetic Route (a) in Synthesis Method 6>

The nucleoside analog (1) (0.33 g, 1.47 mmol) was poured into a flask, and pyridine (7.25 ml) was added for dissolution. Then, DMTrCl (0.54 g, 1.1 eq.) was added and stirred. After 2 hours, disappearance of the raw material was confirmed by TLC. The resulting product was extracted with EtOAc and H$_2$O to recover an organic layer. The organic layer was washed with NaHCO$_3$ aq. and NaCl aq., and the solvent was decompressed and distilled away. The residue was isolated and purified by silica gel column chromatography (neutral silica, CHCl$_3$ to CHCl$_3$:MeOH=100:1). Thus, a compound (24): (S)-5-(5-(bis(4-methoxyphenyl)(phenyl)methoxy)-4-hydroxypent-1-ynyl)-1-methyl pyrimidine-2,4(1H, 3H)-dione (yield: 0.33 g, 43.7%) was obtained.

$^1$H NMR (CDCl$_3$) δ: 8.07 (1H, s) 7.45-7.40, 7.34-7.20, 6.84-6.82 (14H, m) 3.99-3.97 (1H, dd) 3.80 (6H, s) 3.38 (3H, s) 3.26-3.24 (2H, m) 2.70-2.67 (1H, dd) 2.51-2.49 (1H, d, J=5.21)

<6.2. Synthetic Route (b) in Synthesis Method 6>

The compound (24) (0.23 g, 0.44 mmol) was added into a flask, and dissolved in dry THF (2.2 ml) under an argon atmosphere. Then, DIPEA (0.39 ml, 2.20 mmol, 5.0 eq.) and an amidite reagent (0.20 ml, 0.88 mmol, 2.0 eq.) were added and stirred. After 30 minutes, completion of the reaction was confirmed by TLC. Then, the reaction product was extracted with CHCl$_3$ to recover an organic layer. The organic layer was washed with NaHCO$_3$ aq. and NaCl aq., and the solvent was decompressed and distilled away. The residue was purified by silica gel column chromatography (EtOAc:Hexane=1:3). Thus, an amidite body (25) (yield: 0.20 g, 63.7% $^{31}$P NMR (100 MHz) δ: 149.1) was obtained.

Example 7

7. Synthesis of amidite body (32) of nucleoside analog (3): (S)—N'-(5-(5-(bis(4-methoxyphenyl)(phenyl)methoxy)-4-hydroxypent-1-ynyl)pyridin-2-yl)-N,N-dimethylformimidamide 2-cyanoethyl diisopropylphosphoramidite An amidite (32) was synthesized by means of Synthesis method 7 shown in [Chemical Formula 11] below.

23

[Chemical Formula 11]

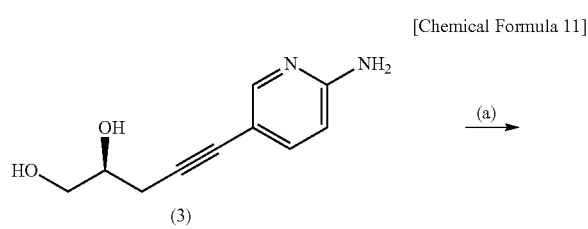

(a) DMF-DMA, DMF (b) DMTrCl, dry pyridine (c) amidite, THF

<7.1. Synthetic Route (a) in Synthesis Method 7>

The nucleoside analog (3) (0.47 g, 1.73 mmol) was poured into a flask, and DMF (17.3 ml) was added for dissolution. Then, DMF-DMA (1.15 ml, 5.0 eq.) was added and stirred at 45° C. overnight. Thereafter, the solvent was decompressed and distilled away. Thus, a compound (30): (S)—N'-(5-(4,5-dihydroxypent-1-ynyl)pyridin-2-yl)-N, N-dimethylformimidamide was obtained.

<7.2. Synthetic Route (b) in Synthesis Method 7>

The compound (30) (1.73 mmol) was added into a flask, and dissolved in pyridine (25 ml). Then, DMTrCl (0.64 g, 1.1 eq.) was added and stirred for 5 hours and 30 minutes. The resulting product was extracted with EtOAc and H₂O, and washed with NaHCO₃ aq. and NaCl aq. Then, the washed product was isolated and purified by silica gel column chromatography. Thus, a compound (31): (S)—N'-(5-(5-(bis(4-methoxyphenyl)(phenyl)methoxy)-4-hydroxypent-1-ynyl)pyridin-2-yl)-N, N-dimethylformimidamide was obtained.

<7.3. Synthetic Route (c) in Synthesis Method 7>

An amidite body (32) of the compound (31) was obtained in a manner similar to the Synthesis method of the amidite body (25).

24

Example 8

8. Synthesis of amidite body (21) of nucleoside analog (5): (S)-1-(bis(4-methoxyphenyl)(phenyl)methoxy)-5-(2-((E)-(dimethylamino)methyleneamino)-4-oxo-1,4-dihydropyrimidin-5-yl)pent-4-yn-2-yl 2-cyanoethyl diisopropylphosphoramidite An amidite (21) was synthesized by means of Synthesis method 8 shown in [Chemical Formula 12] below.

[Chemical Formula 12]

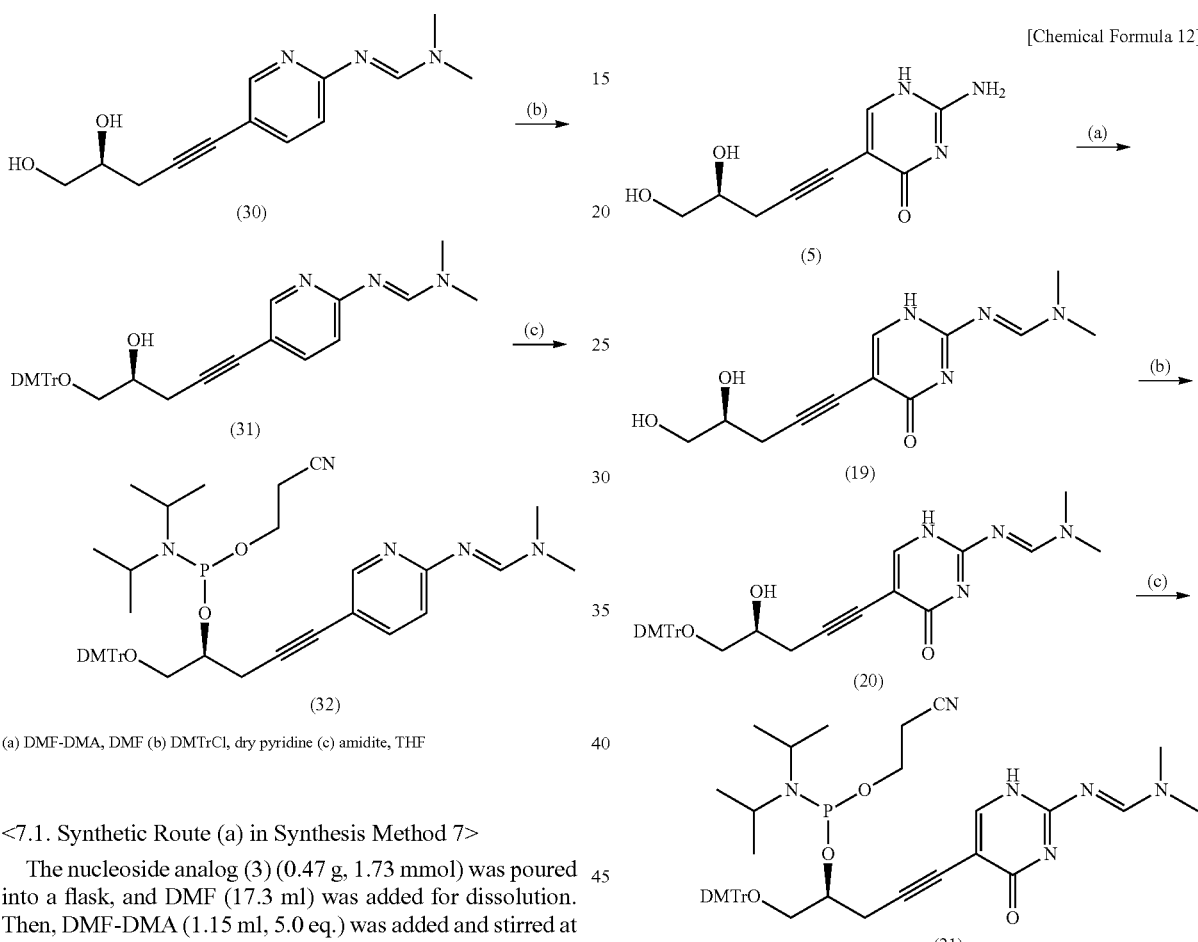

(a) DMF-DMA, dry DMF (b) DMTrCl, dry pyridine (c) i-Pr₂NEt, i-Pr₂NP(Cl)OCE, THF

<8.1. Synthetic Route (a) in Synthesis Method 8>

The nucleoside analog (5) (0.29 g, 1.41 mmol) was poured into a flask under an argon atmosphere, and dissolved in dry DMF (14 ml). In the solution, N, N-dimethylformamid dimethylacetal) (1.12 ml, 8.46 mmol) was added. The mixture was stirred for approximately 5 hours while the temperature was maintained at 40° C. in an oil bath. The reaction solution was decompressed and concentrated using a vacuum evaporator to obtain a compound (19). Thus, the compound (19): (S,E)-N'-(5-(4,5-dihydroxypent-1-ynyl)-4-oxo-1,4-dihydropyrimidin-2-yl)-N,N-dimethylformimidamide was used in the next reaction without post-treatment.

<8.2. Synthetic Route (b) in Synthesis Method 8>

The compound (19) (0.37 g, 1.41 mmol) was poured into a flask, and dissolved in dry pyridine (10 ml) under an argon atmosphere. In the solution, DMTrCl (0.62 g) was added, and stirred for approximately 5 hours. The reaction solution was decompressed and concentrated using a vacuum evaporator. Thus, a compound (20): (S,E)-N'-(5-(5-(bis(4-methoxyphenyl)(phenyl)methoxy)-4-hydroxypent-1-ynyl)-4-oxo-1,4-dihydropyrimidin-2-yl)-N,N-dimethylformimidamide was obtained. The compound (20) was used in the next reaction without post-treatment.

<8.3. Synthetic Route (c) in Synthesis Method 8>

The compound (20) (0.1952 g, 0.344 mmol) was poured into a flask under an argon atmosphere, and dissolved in THF (1.72 ml, 0.2 mol/1). Next, DIPEA (0.36 ml, 2.06 mmol, 6 eq.) was added and stirred, and i-Pr$_2$NP(Cl)OCE (0.15 ml, 2.06 mmol, 2 eq.) was added dropwise. After 1 hour, chloroform was added in the reaction solution to recover an organic layer. The organic layer was washed with saturated sodium hydrogen carbonate and a saturated salt solution, and dried with anhydrous sodium sulfate. Then the solvent was decompressed and distilled away. The residue was isolated and purified by silica gel column chromatography (ethyl acetate only), and the solvent was distilled away. Thus, an amidite body (21) as a yellow crystal was obtained.

Example 9

9. Synthesis of amidite body (102) of nucleoside analog (10): (S)-5-(anthrasen-9-yl)-1-(bis(4-methoxyphenyl)(phenyl)methoxy)pent-4-yn-2-yl 2-cyanoethyl diisopropylphosphoramidite An amidite (101) was synthesized by means of Synthesis method 9 shown in [Chemical Formula 13] below.

[Chemical Formula 13]

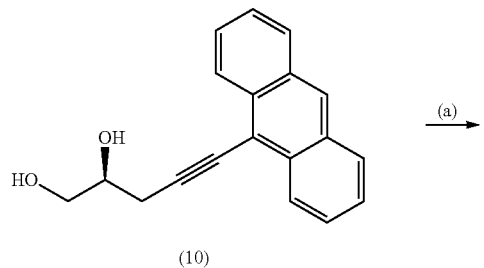

(10)

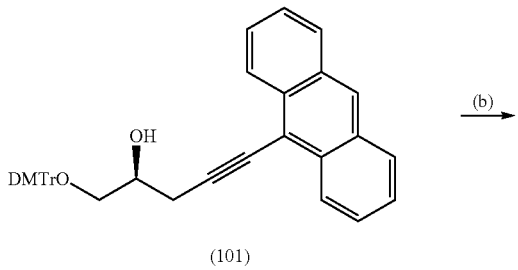

(101)

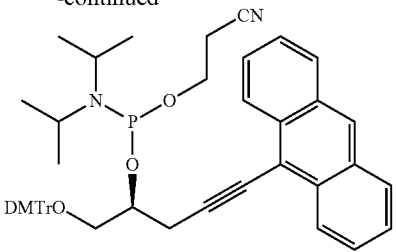

(102)

(a) DMTrCl, dry pyridine (b) DIPEA, i-Pr2NP(Cl)OCE, THF

<9.1. Synthetic Route (a) in Synthesis Method 9>

The nucleoside analog (10) (0.14 g, 0.49 mmol) was poured into a flask, and dissolved in pyridine (2 ml). In the solution, DMTrCl (0.19 g, 0.55 mmol) was poured, and then stirred. After 1 hour, methanol (1 ml) was added to terminate the reaction. The reaction solution was liquid-separated with ethyl acetate, water and NaHCO$_3$ to recover an organic layer. The organic layer was washed with a saturated salt solution, and dried with anhydrous sodium sulfate. The solvent was decompressed and distilled away. The residue was purified by silica gel column chromatography (hexane:ethyl acetate=5:1), and the solvent was decompressed and distilled away. Thus a compound (101): (S)-5-(anthrasen-9-yl)-1-(bis(4-methoxyphenyl)(phenyl)methoxy)pent-4-yn-2-ol (an orange frothy substance, yield: 0.28 g (98%)) was obtained.

$^1$H NMR (400 MHz, CHCl$_3$) δ: 2.57-2.58 (d, 1H, OH, J=4.60 Hz), 3.05-3.07 (d, 2H, C1-H2, J=6.40 Hz), 3.43-3.54 (m, 2H, C3-H2), 3.66 (s, 6H, OMe), 4.20-4.21 (m, 1H, C2-H), 6.75-6.79 (m, 5H, benzene), 7.24-7.50 (m, 13H, benzene), 7.98-8.00 (m, 2H, benzene), 8.39-8.47 (m, 3H, benzene)

<9.2. Synthetic Route (b) in Synthesis Method 9>

The compound (101) (0.26 g, 0.46 mmol) was poured into a flask, and dissolved in THF (2.3 ml). In the solution, DIPEA (0.4 ml) and an amidite reagent (0.21 ml) were added, and stirred at room temperature. After stirring for 45 minutes, the mixture was extracted with chloroform to recover an organic layer. The organic layer was washed with saturated sodium hydrogen carbonate and a saturated salt solution, and dried with anhydrous sodium sulfate. The solvent was decompressed and distilled away, and the residue was purified by silica gel column chromatography (hexane:ethyl acetate=1:1). Thus, a compound (102): (S)-5-(anthrasen-9-yl)-1-(bis(4-methoxyphenyl)(phenyl)methoxy)pent-4-yn-2-yl 2-cyanoethyl diisopropylphosphoramidite (an orange frothy substance, yield: 0.28 g (78%)) was obtained.

$^{31}$P NMR (400 MHz, CDCl$_3$) δ: 149.18

Example 10

10. Synthesis of amidite body (39) of nucleoside analog (11): (S)-1-(bis(4-methoxyphenyl)(phenyl) methoxy)-5-(4-(3-(trifluoromethyl)-3H-diazirin-3-yl)phenyl)pent-4-yn-2-yl cyanomethyl diisopropylphosphoramidite An amidite body (39) was synthesized by means of Synthesis method 10 shown in [Chemical Formula 14] below.

[Chemical Formula 14]

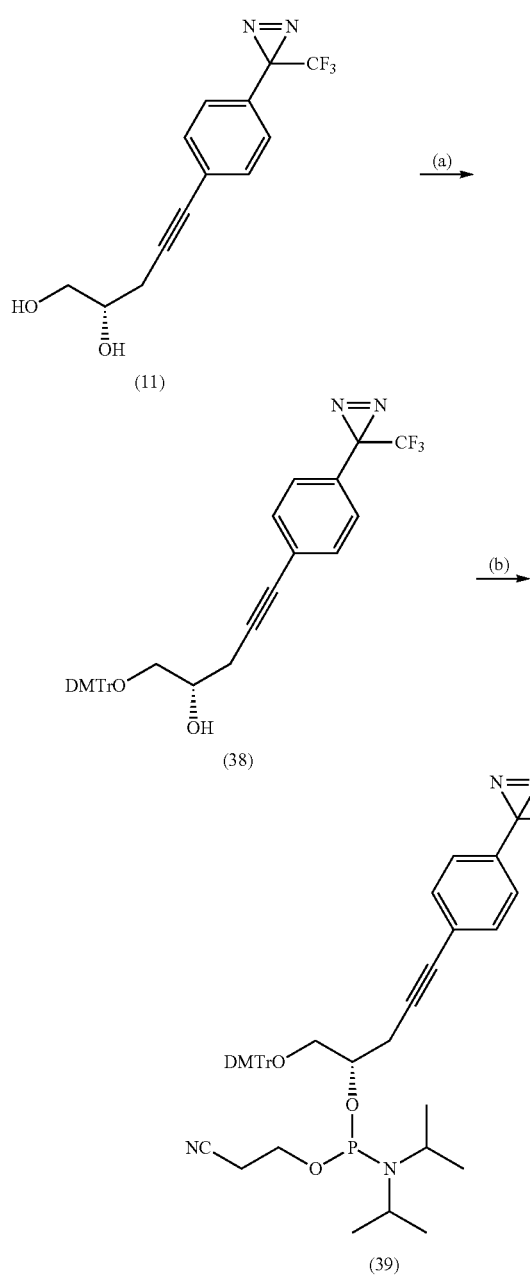

(a) DMTrCl, pyridine, 98% (b) DIPEA, i-Pr₂NP(Cl)OCE, THF, 79%

<10.1. Synthetic Route (a) in Synthesis Method 10>

The nucleoside analog (11) (0.36 g, 1.26 mmol) was poured into a flask under an argon atmosphere, and dissolved in pyridine (7.2 ml). Then DMTrCl (0.47 g, 1.38 mmol, 1.1 eq.) was added little by little under ice-cold conditions. After 5 hours, the resulting mixture was extracted with sat. NaHCO₃ and sat. NaCl, and washed. After drying the organic layer with sodium sulfate, the solvent was decompressed and distilled away. The residue was purified by silica gel column chromatography (hexane:ethyl acetate=2:1). Thus, a compound (38): (S)-1-(bis(4-methoxyphenyl)(phenyl)methoxy)-5-(4-(3-(trifluoromethyl)-3H-diazirin-3-yl)phenyl)pent-4-yn-2-ol (0.73 g, 1.24 mmol, 98%, yellow crystal) was obtained.

$^1$H NMR (400 MHz, CDCl₃) δ: 2.65-2.67 (m, 2H, —OH), 3.63-3.67 (q, 2H), 3.72 (s, 6H, -DMTr), 3.78-3.81 (q, 1H), 3.95-3.97 (m, 2H), 7.08-7.10 (d, 2H), 7.38-7.41 (d, 2H). 6.72-7.47 (m, 16H, DMTr). $^{19}$F NMR (372 MHz, CDCl₃) δ: -81.1 (s, 3F, —CF₃)

<10.2. Synthetic Route (b) in Synthesis Method 10>

The compound (38) (0.73 g, 1.24 mmol) was poured into a flask, and dissolved in THF (6.2 ml, 0.2 mol/1) under an Ar atmosphere. DIPEA (1.08 ml, 6.19 mmol, 5.0 eq.) was added and stirred. Then, i-Pr₂NP(Cl)OCE (0.55 ml, 2.48 mmol, 2.0 eq.) was dropped. After 1 hour, chloroform was added, and sat. NaHCO₃ and sat. NaCl were used for performing extraction and washing to recover an organic layer. After drying the organic layer with sodium sulfate, the solvent was decompressed and distilled away. The residue was isolated and purified by silica gel column chromatography (hexane:ethyl acetate=3:1), and the solvent was distilled away. Thus, an amidite body (39) (0.77 g, 0.98 mmol, 79%, yellow oil form) was obtained.

$^{31}$P NMR (400 MHz, CDCl₃) δ: 149.4 $^{19}$F NMR (372 MHz, CDCl₃) δ: -82.0 (s, 3F, —CF₃)

Example 11

11. Synthesis of CPG Resin-Linked Nucleoside Analog (27)

A CPG resin-linked nucleoside analog (27) was synthesized by means of Synthesis method 11 shown in [Chemical Formula 15] below.

[Chemical Formula 15]

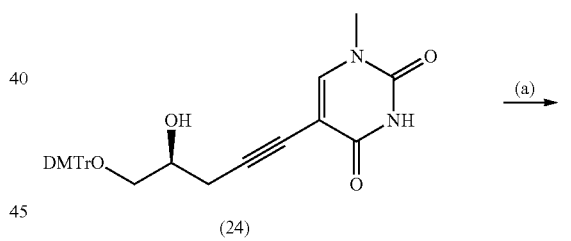

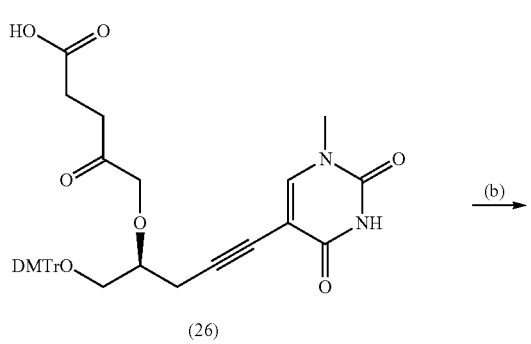

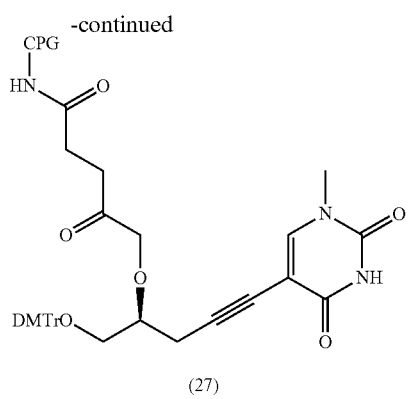

(27)

(a) succinic anhydride, DMAP, pyridine (b) CPG, WSC, DMF

<11.1. Synthetic Route (a) in Synthesis Method 11>

The compound (24) (90 mg, 0.17 mmol) and DMAP (0.42 mg, 0.02 eq.) were poured into a flask, and dissolved in pyridine (1.7 ml). Then, succinic anhydride (50 mg, 3.0 eq.) was added in the solution under an Ar atmosphere, and the mixture was stirred at room temperature. After stirring for 78 hours, the raw material remained. Therefore, DMAP was added in a small amount and stirred. The reaction was terminated next day, and the reaction solution was extracted to recover an organic layer. The organic layer was decompressed and concentrated using a vacuum evaporator. Thus, a succinyl body (26) was obtained.

<11.2. Synthetic Route (b) in Synthesis Method 11>

The succinyl body (26) (113.2 mg, 0.18 mmol) was poured into a flask, and dissolved in DMF (4.5 ml, 0.01 mol/1). Then, a CPG resin (0.38 g, 1.0 eq.) and WSC (34.6 mg, 4.0 eq., 0.18 mmol) were quickly added in the solution, and shaken for 3 days. Thereafter, the CPG resin was washed with pyridine. Subsequently, the resin which did not bond to the succinyl body (26) was capped. The washed resin was added in 0.1 mol/1 DMAP in pyridine (15 ml), and shaken overnight. After confirming that the reaction solution had turned brown, the reaction was terminated. After the reaction was completed, pyridine, EtOH and CH$_3$CN were used in this order to wash the resin. Thus, a CPG resin-linked nucleoside analog (27) (activity: 38.9 μmol/g) was obtained.

Example 12

Calculation of ε Value of Nucleoside Analog (1)

The ε value of the nucleoside analog (1) was calculated in the method shown below.

After dissolving a nucleoside analog (1) (1.12 mg) in MilliQ (50 ml) to produce 0.1 mmol/1 aqueous solution, the absorbance was measured. Then, the ε value was calculated. The result was ε260: 2820 and 68 290: 8630.

The ε260 value of normal thymidine is 7400. However, the nucleoside analog (1) contains alkyne, so that the maximum absorption wavelength was shifted to 293 nm.

Using each CPG resin-linked nucleoside analog or the amidite body of each nucleoside analog, an oligonucleotide analog was synthesized by the solid-phase phosphoramidite method described below.

Example 13

Solid-Phase Phosphoramidite Method

Synthesis of an oligonucleotide analog was performed on 1 μmol scale. A 3400 DNA automated synthesizer was used. A normal phosphoramidite and an amidite of a synthesized analog body were dissolved in MeCN to give 0.1 mol/1 and 0.12 mol/1 respectively, and synthesis was performed using an RNA protocol. The synthesis was completed in a state that a DMTr group was removed at the 5' terminal of an oligonucleotide. A CPG resin was dried through Ar gas. The CPG resin to which the oligonucleotide was bonded was transferred into a sample stock tube, and (NH$_4$OH:EtOH=3:1) was added. The obtained product was shaken at room temperature for 12 hours, thereby to remove the CPG resin. The reaction solution was transferred to an Eppendorf tube, and solid-dried under reduced pressure. Furthermore, TBAF was added in the residue, and the product was subjected to a deprotection treatment of shaking at room temperature for 12 hours. The reaction solution was diluted in 0.1 mol/1 TEAABuf. (30 ml), and the obtained solution was partially purified by C18 reverse phase column chromatography (Sep-Pak). In the residue, 200 μl of loading solution (90% formamide in 1×TBE) was added, and the intended oligonucleotide was isolated by 20% PAGE. The gel band of the intended oligonucleotide was cut out. Then, the gel band was added in each of a 0.1 mol/1 TEAA aqueous solution and a 0.1 mol/1 EDTA aqueous solution (15 ml), and the resulting product was shaken overnight. The filtrate was purified by C18 reverse phase column chromatography (Sep-Pak). The oligonucleotide was dissolved in H$_2$O (1 mL), and absorbance at 260 nm of the obtained diluted solution was measured. Thus, the yield thereof was calculated. The purified oligonucleotide was solid-dried in an amount of 30 pmol, and dissolved in 3 μl of sterile water. Then, after mixing the solution well with 3 μl of a matrix solution, a sample was applied on a plate. After the sample was solid-dried, the structure thereof was identified by MALDI-TOF/MS.

The sequence, the calculated molecular weight (calculated), and the MALDI-TOF/MS measurement result (observed) of each synthesized oligonucleotide analogs are shown in Table 1.

TABLE 1

| | sequence | calculated | observed |
|---|---|---|---|
| Poly T$^a$ | 5'-T$^a$T$^a$T$^a$T$^a$T$^a$T$^a$T$^a$T$^a$T$^a$-3' | 2799.8 | 2799.4 |
| Poly T | 5'-TTTTTTTTTT-3' | 2980.0 | 2978.2 |
| Poly dA | 5'-AAAAAAAAAA-3' | 3070.1 | 3070.2 |
| Poly rA | 5'-r(AAAAAAAAAA)-3' | 3230.1 | 3228.7 |

Here, T$^a$ represents a nucleoside analog (1).

The value which is ten times the ε value of a monomer was used as the ε value of poly T$^a$. The main peak of poly T$^a$ in an MALDI-TOFMS represents the value of 2820.1 as Na adduct.

Example 14

Calculation 1 of Tm Value

In the synthesized oligonucleotide analog, the stability of a double strand with a complementary DNA or RNA was calculated as a Tm value by a thermal denaturation method, and the calculated value was compared to that of a normal double strand (Δ° C.).

Measurement condition: 5 to 85° C., sample concentration of 12 μmol/l, buffer including 10 mmol/1 Na Phosphate and 100 mmol/1 NaCl.

The measured Tms at 260 nm are shown in [FIG. 1] and [Table 2].

TABLE 2

|  | Tm (° C.) | Δ ° C. |
|---|---|---|
| polyTa - dA | 24.6 | 0.8 |
| polyT - dA | 23.8 | — |
| polyTa - rA | 23.6 | 1.1 |
| polyT - rA | 22.5 | — |

As a result, it was found that the Tm value is increased compared to that of the normal thymidine polymer, and that the present analog increases thermal stability of a double strand. This result suggests that the homopolymer of a nucleoside analog (1) is useful as a nanomaterial.

Furthermore, the enthalpy difference (ΔH°) and the entropy difference ΔS° were calculated by the Van't Hoff plot, and the thermodynamic stabilities of the double strands were compared. The results of calculating ΔH° and ΔS° are shown in [Table 3].

R=8.315[kJ/mol], 4.1840 kJ/mol=1 kcal/mol.

TABLE 3

|  | ΔH° [kcal/mol] | ΔS° [cal/mol] |
|---|---|---|
| Poly T - poly rA | −63.3 | −175.3 |
| Poly T - poly dA | −70.8 | −214.7 |
| Poly Ta - poly rA | −55.1 | −163.0 |
| Poly Ta - poly dA | −64.4 | −192.5 |

As a result, it was found that the stabilization of a double strand mainly depends on the entropy term.

Subsequently, base specificity of the analog $T^a$ with RNA was studied. Complementary strands each introduced four types of bases in the center of the strand were prepared. Then, the stabilities of the double strands were compared to each other by measuring Tms.

The sequence, the calculated molecular weight (calculated), and the measurement result of MALDI-TOF/MS (observed) of each synthesized oligonucleotide analog are shown in [Table 4]

TABLE 4

| | sequence | calculated | observed |
|---|---|---|---|
| A-A | 5'-r(GAAGGUCAAUGUAUCUCU)-3' | 7217.0 | 7215.1 |
| A-U | 5'-r(GAAGGUCAUUGUAUCUCU)-3' | 6999.9 | 6998.1 |
| A-C | 5'-r(GAAGGUCACUGUAUCUCU)-3' | 7617.0 | 7624.3 |
| A-G | 5'-r(GAAGGUCAGUGUAUCUCU)-3' | 7400.0 | 7393.9 |
| U-rU | 5'-r(AGAGAUACAUUGACCUUC)-3' | 7586.1 | 7594.1 |
| U-$T^a$ | 5'-r(AGAGAUACAT$^a$UGACCUUC)-3' | 7368.3 | 7363.6 |
| U-2$T^a$ | 5'-r(AGAGAUACAT$^a$T$^a$GACCUUC)-3' | 7586.0 | 7594.1 |

Example 15

Calculation 2 of Tm Value

Figure 2:
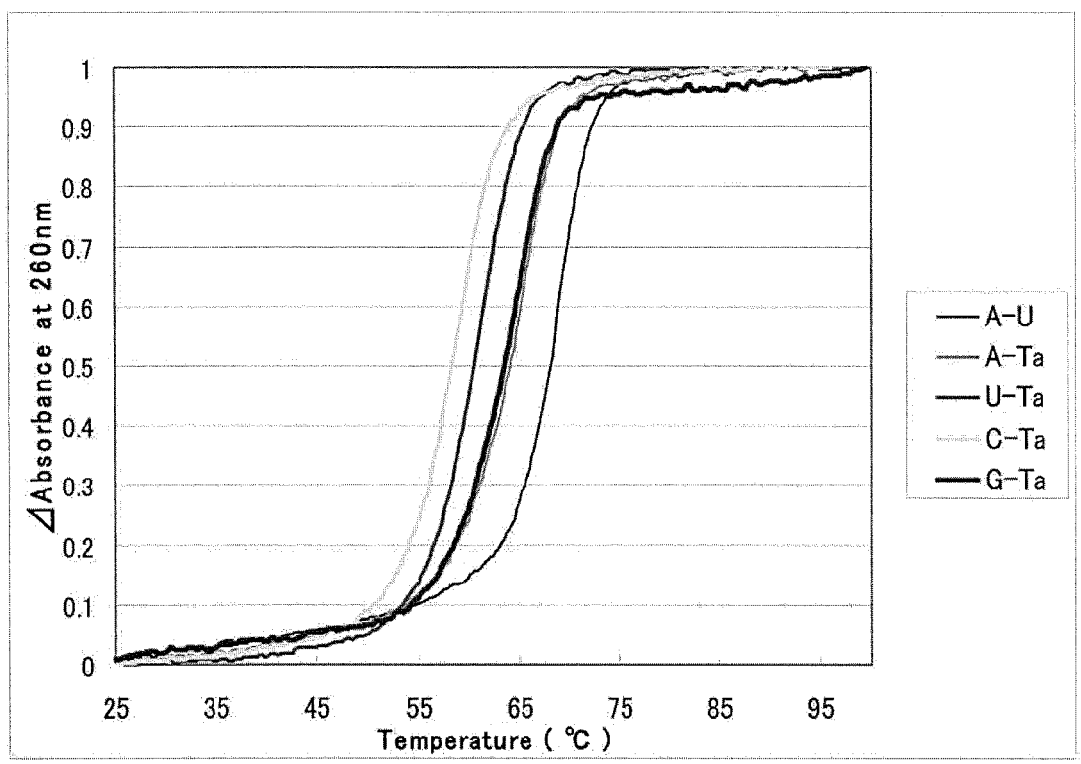
FIG. 2 is a graph illustrating results of Tm measurement.

The results of Tm measurement are shown in [FIG. 2] and [Table 5].

Measurement condition: 20 to 100° C., sample concentration of 3 μmol/l, buffer including 10 mmol/l Na Phosphate and 100 mmol/l NaCl.

TABLE 5

| Tm | Δ ° C. |
|---|---|
| A-U: 67.9 | — |
| A-Ta: 64.3 | −3.6 |

TABLE 5-continued

| Tm | Δ ° C. |
|---|---|
| U-Ta: 60.8 | −7.1 |
| C-Ta: 58.6 | −9.3 |
| G-Ta: 63.7 | −4.2 |

Furthermore, the Tms of the oligonucleotide analogs each substituted two bases with the nucleoside analog (1) were measured.

Example 16

Calculation 3 of Tm Value

Figure 3:
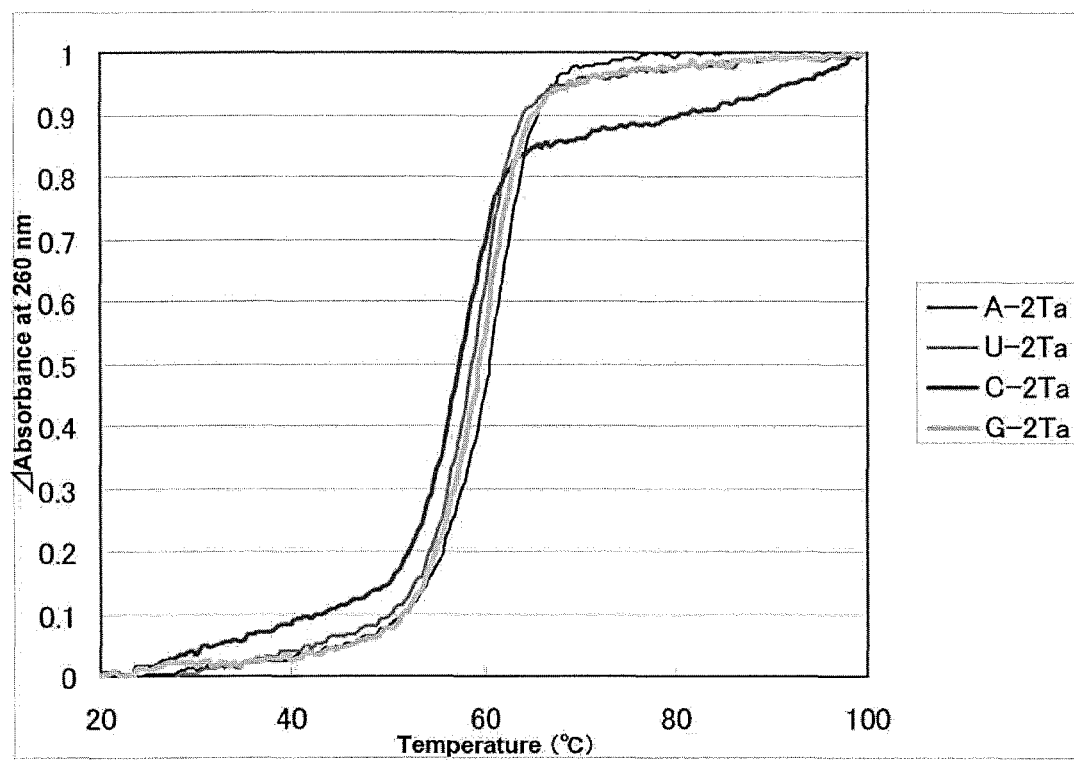
FIG. 3 is a graph illustrating results of Tm measurement.
In FIGS. 4A and 4B.

The results of Tm measurement are shown in [FIG. 3] and [Table 6].

TABLE 6

| Tm | Δ ° C. |
|---|---|
| A-2Ta: 60.9 | −7.0 |
| U-2Ta: 59.1 | −8.8 |
| C-2Ta: 57.5 | −10.4 |
| G-2Ta: 59.7 | −8.2 |

As seen from the above results, the sugar-part ring-opened nucleoside analog (1) introduced in the center of the chain has a hydrogen bond with a normal base. That is, the nucleoside analog (1) has base specificity. However, the nucleoside analog (1) causes thermal stability of a double strand to decrease.

Furthermore, 18mer oligonucleotide each introduced a synthesized cytosine analog Cz: nucleoside analog (5) in the oligonucleotide and complementary strands thereof were synthesized. The sequence, the calculated molecular weight (calculated), and the measurement result of MALDI-TOF/MS (observed) of each synthesized oligonucleotide analog are shown in [Table 7].

TABLE 7

| name | sequence | calculated | observed |
|---|---|---|---|
| CZ1-ss | 5'-d(GAAGGTCAAC$_Z$GTATCTCT)-3' | 5480.6 | 5474.9 |
| CZ2-ss | 5'-d(GAAGGTCAAC$_Z$C$_Z$TATCTCT)-3' | 5422.5 | 5422.5 |
| CZ3-ss | 5'-d(GAAGGTCAC$_Z$C$_Z$C$_Z$TATCTCT)-3' | 5380.5 | 5382.5 |
| normal-as | 5'-d(AGAGATAGGTTGACCTTC)-3' | 5538.6 | 5537.9 |
| normal-as | 5'-d(AGAGATAGGGTGACCTTC)-3' | 5563.6 | 5563.1 |

Furthermore, the oligonucleotide analogs synthesized using the sequences shown below and the existing oligonucleotides were combined as shown below. Then, the Tm values thereof were measured for comparison. The results of Tm measurement are shown in [Table 8].

TABLE 8

| sample | | Sequence | Tm value |
|---|---|---|---|
| 1 | sense | 5'-d(GAAGGTCAATGTATCTCT)-3' | 56.7 |
| | antisense | 3'-d(CTTCCAGTTACATAGAGA)-5' | |
| 2 | sense | 5'-d(GAAGGTCAAC$_Z$GTATCTCT)-3' | 49.7 |
| | antisense | 3'-d(CTTCCAGTTACATAGAGA)-5' | |
| 3 | sense | 5'-d(GAAGGTCAAC$_Z$GTATCTCT)-3' | 50.7 |
| | antisense | 3'-d(CTTCCAGTTCCATAGAGA)-5' | |
| 4 | sense | 5'-d(GAAGGTCAAC$_Z$GTATCTCT)-3' | 53.3 |
| | antisense | 3'-d(CTTCCAGTTTCATAGAGA)-5' | |

TABLE 8-continued

| sample | | Sequence | Tm value |
|---|---|---|---|
| 5 | sense | 5'-d(GAAGGTCAAC$_Z$GTATCTCT)-3' | 59.2 |
|   | antisense | 3'-d(CTTCCAGTTGCATAGAGA)-5' | |
| 6 | sense | 5'-d(GAAGGTCAATGTATCTCT)-3' | 54.2 |
|   | antisense | 3'-r(CUUCCAGUUACAUAGAGA)-5' | |
| 7 | sense | 5'-d(GAAGGTCAAC$_Z$GTATCTCT)-3' | 47.5 |
|   | antisense | 3'-r(CUUCCAGUUACAUAGAGA)-5' | |
| 8 | sense | 5'-d(GAAGGTCAAC$_Z$GTATCTCT)-3' | 51.2 |
|   | antisense | 3'-r(CUUCCAGUUCCAUAGAGA)-5' | |
| 9 | sense | 5'-d(GAAGGTCAAC$_Z$GTATCTCT)-3' | 52.1 |
|   | antisense | 3'-r(CUUCCAGUUUCAUAGAGA)-5' | |
| 10 | sense | 5'-d(GAAGGTCAAC$_Z$GTATCTCT)-3' | 56.6 |
|   | antisense | 3'-r(CUUCCAGUUGCAUAGAGA)-5' | |
| 11 | sense | 5'-d(GAAGGTCAAC$_Z$C$_Z$TATCTCT)-3' | 57.0 |
|   | antisense | 3'-d(CTTCCAGTTGGATAGAGA)-5' | |
| 12 | sense | 5'-d(GAAGGTCAC$_Z$C$_Z$C$_Z$TATCTCT)-3' | 58.7 |
|   | antisense | 3'-d(CTTCCAGTGGGATAGAGA)-5' | |

From the above results, it was found that the synthesized sugar-part ring-opened cytosine analog Cz: nucleoside analog (5) can select a mismatch to form a hydrogen bond with a complementary strand. Furthermore, there was obtained the result that the thermodynamic stability is similar to or superior to that of a normal nucleoside. Even when the number of the sugar-part ring-opened cytosine analogs Cz: nucleoside analogs (5) introduced in the center of the sequence is increased to two, or three, the Tm value was not significantly changed.

[Application to miR199a]

MiR199a has a sequence that targets HCV (Hepatitis C virus). Therefore, it will be reviewed whether a sugar-part ring-opened nucleoside analog can be applied to miRNA, and can be utilized in order to improve guide strand selectivity. Even if one or two of the used nucleoside analog (1): analog $T^\alpha$ are introduced, the Tm value will decrease. Therefore, it is considered that the number of the analogs to be introduced in miR199a is up to one per strand. Also, the gene expression inhibiting abilities differ depending on a psi199a5p vector or a psi199a3p vector. The reasons why use of the psi199a3p vector especially increase the expression inhibition are considered that existence of adenosine at the 5' terminal facilitates formation of RISC; and existence of a bulge-out region at two locations in miR199a5p facilitates dissociation of a double strand into a single strand. Another reason is considered that, since a lot of AU base pairs are contained on the 5' terminal side of miR199a3p while GC base pairs dominantly exist on the 5' terminal side of miR199a5p, thermodynamic stability was imbalanced.

Since it is considered that guide selectivity depends on various factors, it was decided to investigate on which region in the analog is most effective to introduce miR199a5p. For this purpose, one base U was substituted with $T^\alpha$ in each of miR199a5p and miR199a3p, so that 14 miRNAs were synthesized in total, and used for assay.

Example 17

Investigation of Gene Expression Inhibiting Abilities of miRNA199a

In miR199a3p and miR199a5p each having a sequence that targets HCV, U in a varied region was substituted with the nucleoside analog (1): analog $T^\alpha$ (indicated as Y in [Table 9]). Changes caused by the nucleoside analog (1) in gene expression inhibiting abilities, which is specific to the modified region of miRNA199a, were investigated.

The sequences of the synthesized oligonucleotides were shown below.

TABLE 9

| | Sequence |
|---|---|
| miR199a5p - <1> | 5'-CCCAGYGUUCAGACUACCUGUUC-3' |
| miR199a5p - <3> | 5'-CCCAGUGUYCAGACUACCUGUUC-3' |
| miR199a5p - <4> | 5'-CCCAGUGUUCAGACYACCUGUUC-3' |
| miR199a5p - <6> | 5'-CCCAGUGUUCAGACUACCUGYUC-3' |
| miR199a3p - <3> | 5'-ACAGUAGUCUGCACAUYGGUUA-3' |
| miR199a3p - <5> | 5'-ACAGUAGUCYGCACAUUGGUUA-3' |
| miR199a3p - <7> | 5'-ACAGYAGUCUGCACAUYGGUUA-3' |
| miR199a5p | 5'-CCCAGUGUUCAGACUACCUGUUC-3' |
| miR199a3p | 5'-ACAGUAGUCUGCACAUUGGUUA-3' |

Using the synthesized oligonucleotide analogs (miRNA<1>, miRNA<2>, miRNA<3>, miRNA<4>, miRNA<5>, miRNA<6>, miRNA<7> and miRNA<8>), gene expression inhibiting abilities were investigated.

The gene expression inhibiting abilities were evaluated by introducing miRNA<1> to miRNA<8> into respective HeLa cells and performing the Dual-Luciferase reporter assay.

The data regarding miRNA<1> to miRNA<8> are shown in [Table 10]. The miR in [Table 10] represents miRNA. In the table, 5p is a miRNA derived from the arm on the 5' side of a pre-miRNA, and 3p is a miRNA derived from the arm on the 3' side of a pre-miRNA.

TABLE 10

| | miR199a5p | miR199a3p |
|---|---|---|
| miRNA<1> | Normal | Normal |
| miRNA<2> | 5p<1> | Normal |
| miRNA<3> | 5p<3> | Normal |
| miRNA<4> | 5p<4> | Normal |
| miRNA<5> | 5p<6> | Normal |
| miRNA<6> | Normal | 3p<3> |
| miRNA<7> | Normal | 3p<5> |
| miRNA<8> | Normal | 3p<7> |

The miRNA<1> is formed with a normal miR199a5p and a normal miR199a3p. The miRNA<2> is formed with a miR199a5p-<1> and a normal miR199a3p. The miRNA<3> is formed with a miR199a5p-<3> and a normal miR199a3p. The miRNA<4> is formed with a miR199a5p-<4> and a normal miR199a3p. The miRNA<5> is formed with a miR199a5p-<6> and a normal miR199a3p. The miRNA<6> is formed with a normal miR199a5p and a miR199a3p-<3>. The miRNA<7> is formed with a normal miR199a5p and a miR199a3p-<5>. The miRNA<8> is formed with a normal miR199a5p and a miR199a3p-<7>.

Figure 4A:
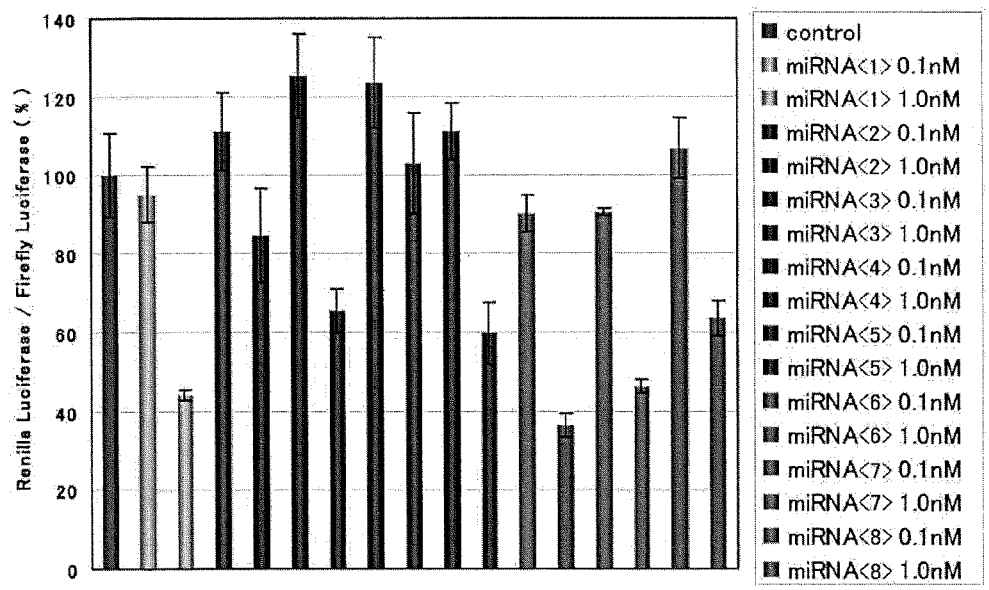
FIG. 4A is a graph illustrating results of investigating gene expression inhibiting abilities when a psi199a3p vector is used.
Figure 4B:
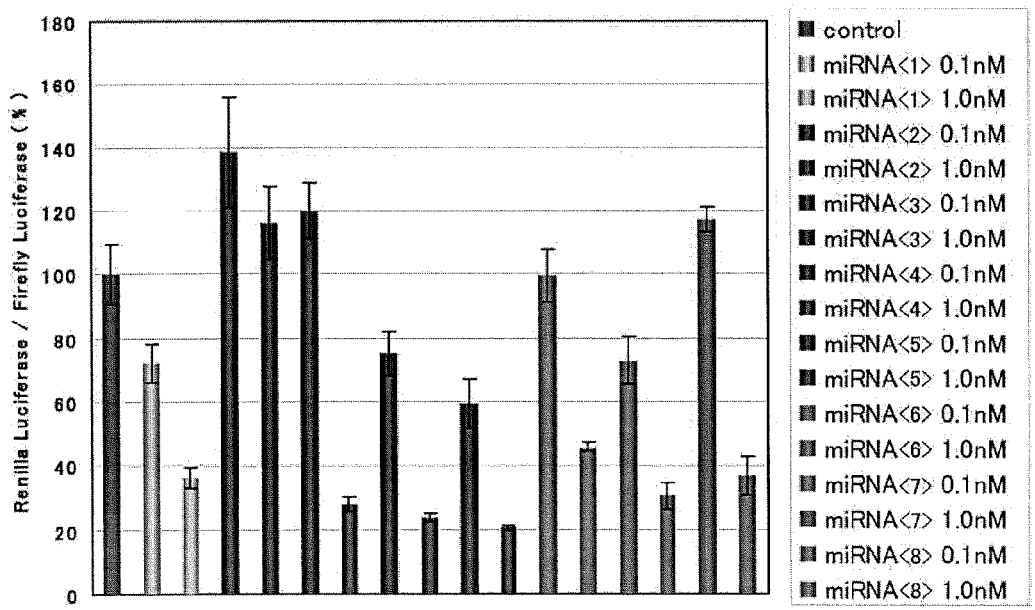
FIG. 4B is a graph illustrating results of investigating gene expression inhibiting abilities when a psi199a5p vector is used.
In FIGS. 5A and 5B.

The results of investigating gene expression inhibiting abilities are shown in [FIGS. 4A and 4B]. It was found that the gene expression inhibiting abilities of the miRNA which contains a sugar-part ring-opened nucleoside analog (1): analog $T^\alpha$ as a component have specificity depending on the modified region of miRNA. The miRNA<2> did not significantly inhibit expression with either of the vectors. The miRNA<4> and <5> introduce the analog $T^\alpha$ on the 3' terminal side, thereby to be destabilized. Accordingly, the 5' terminal side of its reverse strand is destabilized so as to be incorporated as a guide strand. Therefore, it is considered that the expression inhibiting abilities are improved compared to the normal miRNA, and expression inhibition by a reverse strand can be suppressed. Also, the miRNA<3> having a modification in the bulge-out region has the expression inhibiting abilities superior to that of the normal miRNA, but its reverse strand inhibits expression to some extent as well. The miRNA<6> is observed to have some strand selectivity for the same reasons to in miRNA<4> and <5>, but the degree of the strand selectivity is small. The miRNA<7> and <8> also show expression inhibition to the same level as in the normal miRNA, but the expression inhibition caused by its reverse strand is observed to some extent. From the above results, it is considered that strand selectivity can be obtained without reducing expression inhibiting abilities, by introducing a modification on the 3' terminal side to incorporate its reverse strand in RISC, rather than introducing a modification on the 5' terminal side to be destabilized.

Example 18

Investigation of Nuclease Resistance

With respect to the miRNA containing the nucleoside analog (1) as a component, stability was studied by snake venom phosphodiesterase (SVP). The miRNA containing the nucleoside analog (1) as a component is a single-stranded RNA in which dT (thymidine) in the 3'-overhang is substituted with the nucleoside analog (1). The miRNA containing the nucleoside analog (1) as a component was treated with the SVP in a time-dependent manner. After the reaction was terminated, the degraded RNA fragments were analyzed by electrophoresis.

Figure 5A:
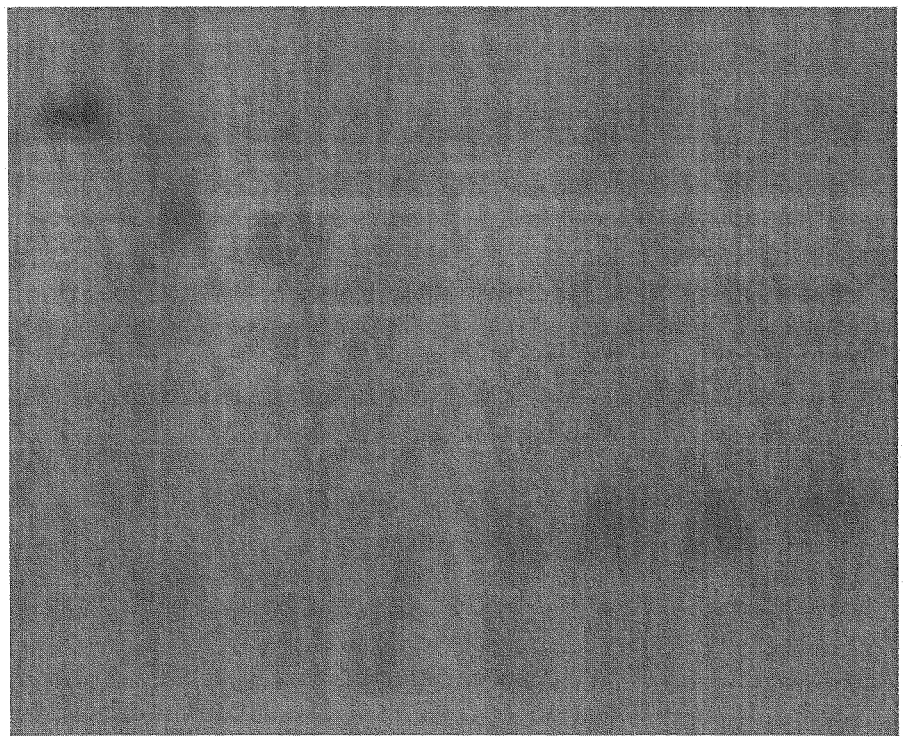
FIG. 5A is a gel photograph after electrophoresis for investigating nuclease resistance of a normal RNA.
Figure 5B:
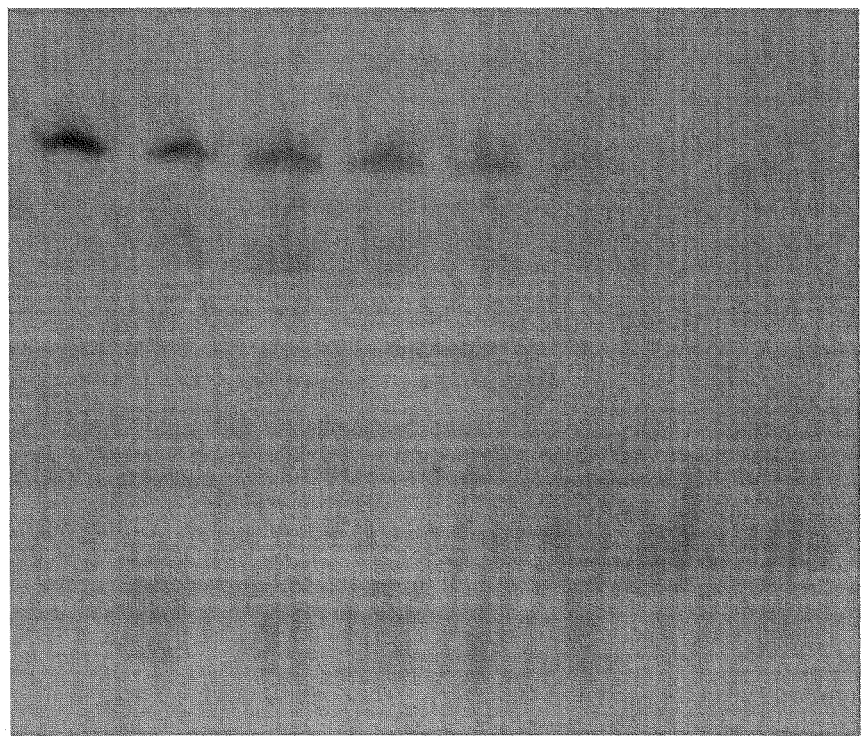
FIG. 5B is a gel photograph after electrophoresis for investigating nuclease resistance of an RNA having a 3' terminal substituted with a nucleoside analog (1).
Figure 6:
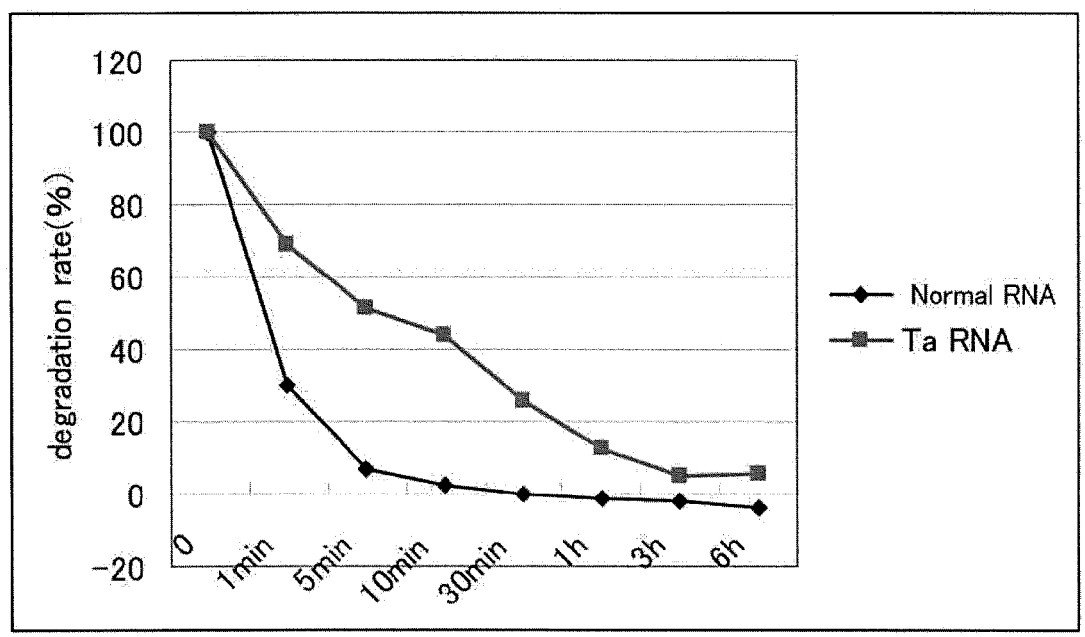
FIG. 6 is a graph illustrating results of investigating the nuclease resistance of a normal RNA and the nuclease resistance of an RNA having a 3' terminal substituted with a nucleoside analog (1).

The analysis results are shown in [FIGS. 5A to 5B] and [FIG. 6]. The Ta RNA in [FIG. 6] is a miRNA containing the nucleoside analog (1): $T^a$ as a component.

The RNAs remained without being degraded are shown in a time-dependent manner (from the right side, 0 min, 1 min, 5 min, 10 min, 30 min, 1 h, 3 h, and 6 h). The RNA concentration during an enzyme reaction is 1 μmol/l. Although the buffer used in the enzyme reaction system is not limited as long as it is a buffer suitable for the enzyme, a tris-hydrochloric acid buffer was used. After a certain time has passed, ethylenediaminetetraacetic acid (EDTA) was added, and heated at 100° C. for 2 minutes to terminate the reaction. The reaction solution after reaction was investigated by gel electrophoresis, and the survival rate of RNAs remaining without being degraded was measured using reverse-phase high performance liquid chromatograph (HPLC).

From the above results, as shown in [FIG. 6], it was found that the miRNA containing a nucleoside analog (1); $T^a$ as a component remains without being degraded at a ratio of 50% or more even after 5 minutes have passed, as compared to the normal miRNA; and that the stability is increased by containing the nucleoside analog (1) as a component.

Example 19

Application to Nucleic Acid Probe of miRNA

Using a miRNA containing a nucleoside analog (11) as a component, it was investigated whether or not its complementary strand can be captured by light irradiation, taking advantage of the fact that the nucleoside analog (11) is a photoreactive residue.

The miRNA containing a nucleoside analog (11) as a component was defined as No.2. The complementary strand RNAs, in which the bases to be paired with the nucleoside analog (11) were changed, were defined as No.6, No.7 and No.8. Each of the complementary strand RNAs was annealed with No.2.

Thereafter, under a condition of 0° C., each of the annealed samples was irradiated with UV at 365 nmm to initiate a cross-coupling reaction. A 5 μml aliquot of the sample was taken at each time interval, and a 7 mol/l urea solution (4 μml) and a loading buffer (4 μml) were added to terminate the reaction. After the reaction was terminated, investigation was performed by denaturing gel electrophoresis.

Figure 7:
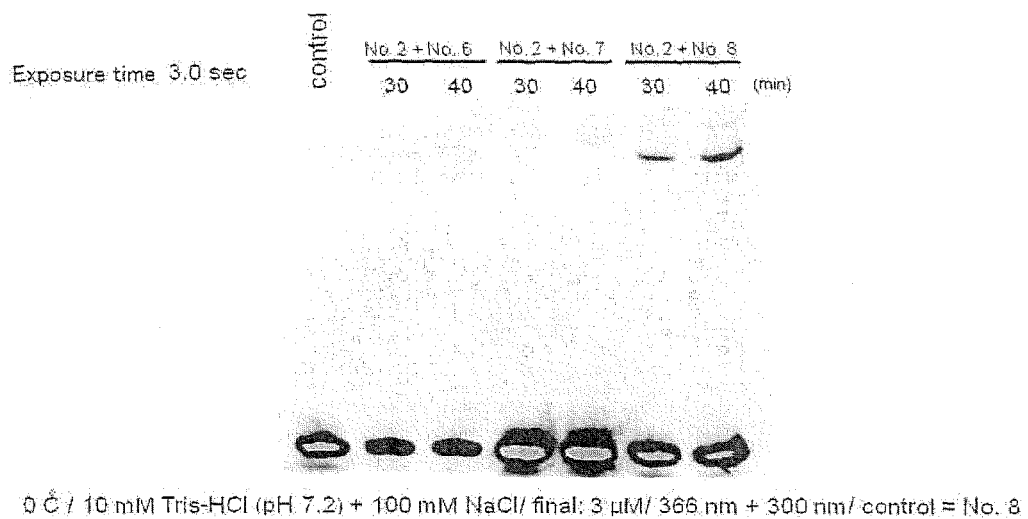
FIG. 7 is a gel photograph after electrophoresis illustrating results of cross coupling.

The sequences of No.2, No.6, No.7 and No.8 are shown in [Table 11]. The results of cross-coupling reaction between No.2 and each RNA are shown in [FIG. 7].

TABLE 11

| No. 2 | 5'-r (UGA GGU AGU XGGUUG UAU AGU)-3' |
| No. 6 | 3'-r (ACU CCA UCA UCC AAC AUA UCA)-F-5' |
| No. 7 | 3'-r (ACU CCA UCA UCA AAC AUA UCA)-F-5' |
| No. 8 | 3'-F-r (ACU CCA UCA ACC AAC AUA ACA)-5' |

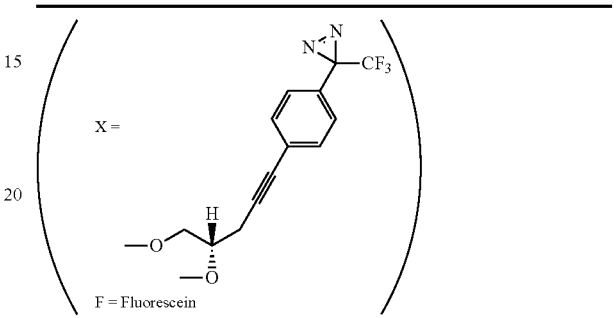

Figure 8:
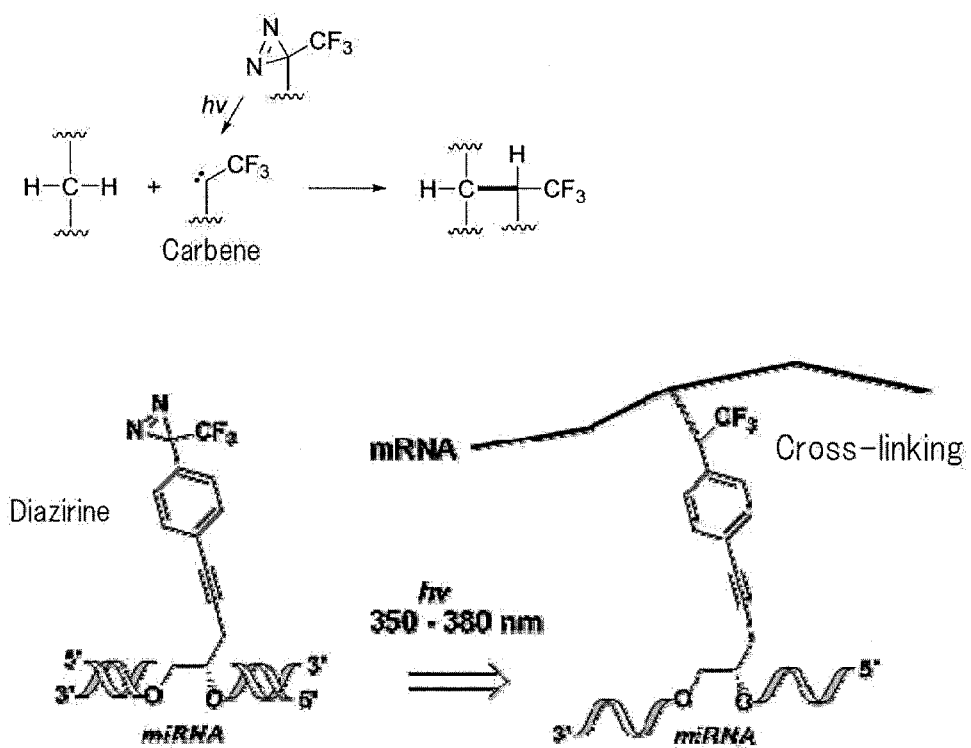
FIG. 8 is an illustrative view of the nucleic-acid probe for detecting gene according to the present invention.

From the above results, it was found that especially the cross-coupling reaction between RNA No.2 and RNA No.8 significantly occurs. This result suggests that the miRNA containing a nucleoside analog (11) as a component can capture an mRNA in a sequence-specific manner. Thus, it is considered that the base sequence of an mRNA targeted by a miRNA can be determined by capturing an mRNA targeted by a miRNA (see FIG. 8) and studying the sequence of the captured mRNA.

Other Embodiments

Although the embodiments of the present invention have been described above, the present invention is not limited to the above-described embodiment, and can be implemented in other various embodiments.

For example, an siRNA containing one of the nucleoside analogs (1) to (11) as a component can be synthesized.

The sequences of the synthesized siRNAs are shown below. The synthesized single-stranded siRNAs are 21mer RNAs each containing the nucleoside analog (1) as a component, and 22mer RNAs each containing the nucleoside analog (10) as a component.

The sequences of the 21mer RNAs each containing the nucleoside analog (1) as a component is shown in Table 12. In ON1 and ON2, thymidine is introduced in the dangling-end region at the 3' terminal. In ON3 and ON4, the nucleoside analog (1) is introduced in the dangling-end region at the 3' terminal. In ON8, the nucleoside analog (1) is introduced on the 5' terminal end, and thymidine is introduced in the dangling end region at the 3' terminal. In ON9, the nucleoside analog (1) is introduced on the 3' terminal side, and thymidine is introduced in the dangling end region at the 3' terminal.

TABLE 12

| RNA | Sequence |
|---|---|
| ON1 | 5'-CUUCUUCGUCGAGACCAUGtt-3' |
| ON2 | 5'-CAUGGUCUCGACGAAGAAGtt-3' |
| ON3 | 5'-CUUCUUCGUCGAGACCAUGT$^a$T$^a$-3' |
| ON4 | 5'-CAUGGUCUCGACGAAGAAGT$^a$T$^a$-3' |

TABLE 12-continued

| RNA | Sequence |
| --- | --- |
| ON8 | 5'-CT$^a$UCUUCGUCGAGACCAUGtt-3' |
| ON9 | 5'-CUUCUUCGUCGAGACCAT$^a$Gtt-3' |

Furthermore, the synthesized single-stranded 21mer siRNA is, as shown in [Table 13], combined with the sequence of its complementary strand to form a double strand.

TABLE 13

| siRNA | sense | antisense |
| --- | --- | --- |
| siRNA<1> | ON1 | ON2 |
| siRNA<2> | ON3 | ON4 |
| siRNA<6> | ON8 | ON2 |
| siRNA<7> | ON9 | ON2 |

The siRNA<1> is a normal siRNA, the ON1 is a sense strand of the siRNA<1> and the ON2 is an antisense strand of the siRNA<1>. The ON3 is a sense strand of the siRNA<2> and the ON4 is an antisense strand of the siRNA<2>. The ON8 is a sense strand of the siRNA<6> and the ON2 is an antisense strand of the siRNA<6>. The ON9 is a sense strand of the siRNA<7> and the ON2 is an antisense strand of the siRNA<7>.

The sequences of 22mer siRNAs each containing the nucleoside analog (10) as a component are shown in Table 14. In each of sense and antisense, a nucleoside analog (10;E) is introduced on the 5' terminal side.

TABLE 14

| RNA | sequence | calculated | observed | OD |
| --- | --- | --- | --- | --- |
| normal-sense | 5'-CUUCUUCGUCGAGACCAUGtt-3' | 6921.3 | 6922.4 | 1.40 |
| normal-antisense | 5'-CAUGGUCUCGAUGAAGAAGtt-3' | 7071.4 | 7071.2 | 4.39 |
| sense | 5'-ECUUCUUCGUCGAGACCAUGtt-3' | 6921.3 | 6922.4 | 4.11 |
| antisense | 5'-ECAUGGUCUCGAUGAAGAAGtt-3' | 7071.4 | 7071.2 | 4.00 |

Figure 9:
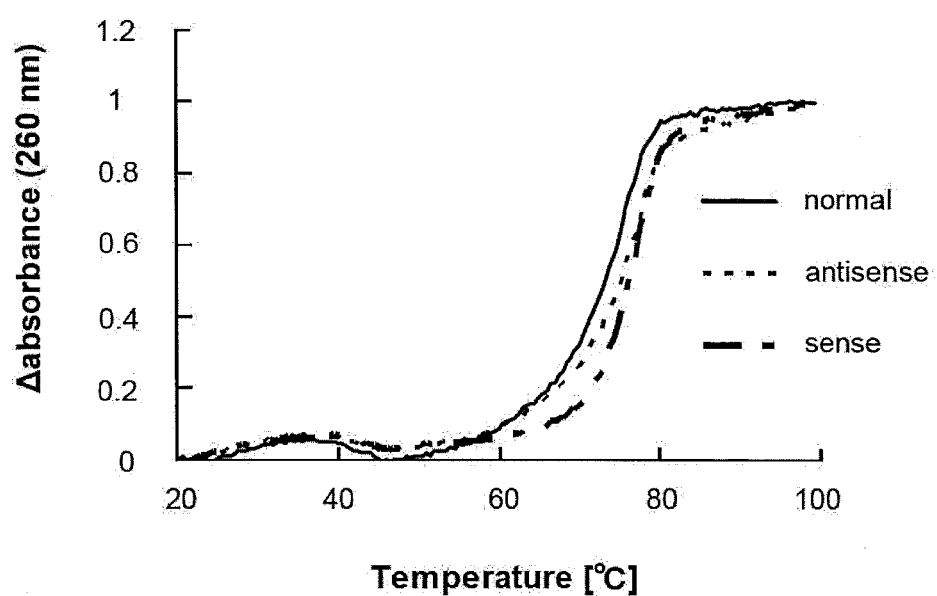
FIG. 9 is a graph illustrating results of Tm measurement.

Furthermore, the synthesized single-stranded 22mer siRNA is, as shown in [Table 15], combined with the sequence of its complementary strand to form a double strand. In the siRNAsense, the sense strand is sense, and the antisense strand is a normal antisense. In the siRNAantisense, the sense strand is a normal sense, and the antisense strand is antisense. The results of Tm measurement are shown in [FIG. 9] and [Table 15].

TABLE 15

| siRNA | RNA | sequence | Tm value[° C.] |
| --- | --- | --- | --- |
| native | normal-sense | 5'-CUUCUUCGUCGAGACCAUGtt-3' | 72.2 |
|  | normal-antisense | 5'-CAUGGUCUCGAUGAAGAAGtt-3' |  |
| sense | sense | 5'-ECUUCUUCGUCGAGACCAUGtt-3' | 76.2 |
|  | normal-antisense | 5'-CAUGGUCUCGAUGAAGAAGtt-3' |  |
| antisense | normal-sense | 5'-CUUCUUCGUCGAGACCAUGtt-3' | 74.2 |
|  | antisense | 5'-ECAUGGUCUCGAUGAAGAAGtt-3' |  |

From the results of Tm measurement, it was found that the Tm values of both the siRNA containing as a component the nucleoside analog (10) on the 5' terminal side of the sense strand and the siRNA containing as a component the nucleoside analog (10) on the 5' terminal side of the antisense strand are increased compared to the normal siRNA, and that the nucleoside analog (10) increases thermal stability of a double strand.

[Investigation of Gene Expression Inhibiting Abilities]

With respect to siRNA<1>, siRNA<2>, siRNA<6> and siRNA<7> disclosed in [Table 13] and siRNAsense and siRNAantisense disclosed in [Table 15], gene expression inhibiting abilities were investigated.

For investigating the gene expression inhibiting abilities, a Psi check vector was used. The samples were prepared so that each siRNA becomes 0.1, 1.0, and 10 nmol/1, and the prepared samples were transfected into HeLa cells. Then, the Dual-Luciferase reporter assay was performed for investigation. The results of the gene expression inhibiting abilities of siRNA<1>, siRNA<2>, siRNA<6>, and siRNA<7> are shown in [FIG. 10], and the results of the gene expression inhibiting abilities of siRNAsense and siRNAantisense are shown in [FIG. 11].

Figure 10:
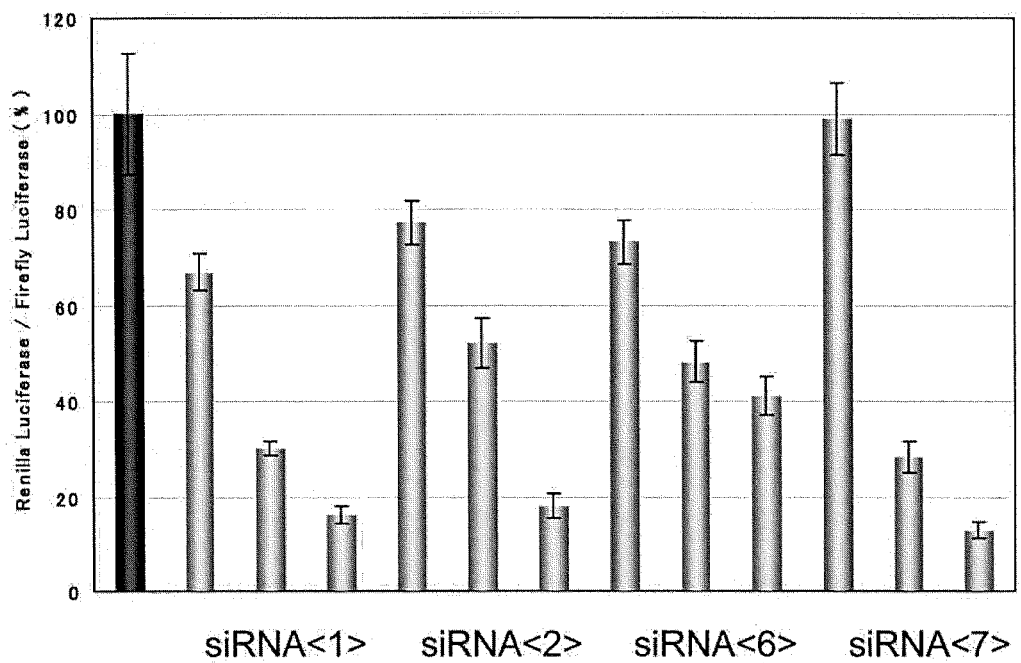
FIG. 10 is a graph illustrating results of investigating gene expression inhibiting abilities of a siRNA containing a nucleoside analog (1) as a component.

As shown in [FIG. 10], siRNA<2> presented gene expression inhibiting abilities to the same level as those of a normal siRNA<1>, but when the concentration of the sample is low, the gene expression inhibiting abilities become lower than those of a normal siRNA<1>. Also, it was shown that the gene expression inhibiting abilities of siRNA<6> are decreased compared to those of a normal siRNA. It is considered this is because the introduction of a nucleoside analog (1) on the 5' terminal side of a sense strand in siRNA<6> causes a double strand to become unstable, thereby facilitating incorporation of the sense strand. Furthermore, it was found that the siRNA<7> has high gene expression inhibiting abilities compared to a normal siRNA. It is considered that this is because introduction of a nucleoside analog (1) on the 3' terminal side of a sense strand in the siRNA<7> causes the 5' terminal side of an anti-sense strand to be destabilized, thereby facilitating incorporation of the anti-sense strand.

Figure 11:
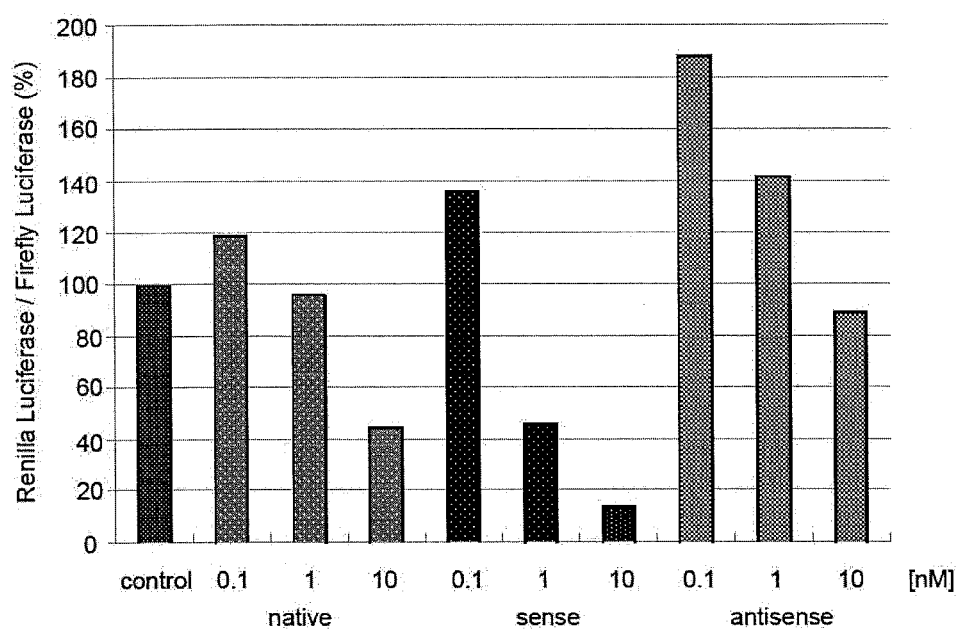
FIG. 11 is a graph illustrating results of investigating gene expression inhibiting abilities of an siRNA containing a nucleoside analog (10) as a component.

Also, as shown in [FIG. 11], it was found that the gene expression inhibiting abilities of a siRNAsense are increased compared to a normal siRNAnative when the concentration of a sample is high. It was found that the gene expression inhibiting abilities of a siRNAantisense are decreased compared to a normal siRNAnative.

In the above-described embodiments, the nucleoside analogs (1), (3), (5), (10) and (11) were illustrated as examples of the nucleoside analogs represented by the general formulae (1), (3), (5), (10) and (11), and the synthesis methods thereof were described in detail. However, even if some of the groups are different from those of the illustrated nucleoside analogs (1), (3), (5), (10) and (11), such nucleoside analogs can be expected to have a similar operation and effect, as long as the nucleoside analogs are nucleoside analogs represented by the general formulae (1), (3), (5), (10) and (11). Also, the synthesis methods of such nucleoside analogs are almost similar to the procedures for the illustrated nucleoside analogs (1), (3), (5), (10) and (11).

Also, each of the nucleoside analogs (2), (4), (6), (7), (8) and (9) can be synthesized almost similarly to the procedures for the illustrated nucleoside analogs (1), (3), (5), (10) and (11), merely by applying starting materials having molecular structures corresponding to the base parts of these nucleoside analogs.

More particularly, a sugar part including a hydroxyl group protected with a silyl group and a base part having a halogen substituent are subjected to a coupling reaction in the presence of a palladium catalyst, to obtain a coupling body. Thereafter, a deprotection reaction of the protecting group and a purification process are performed. Thus, the nucleoside analog having a structure represented by any of the general formulae (2), (4), (6), (7), (8) and (9) can be synthesized.

Furthermore, the effect of a siRNA containing as a component one or more structures represented by any of the general formulae (2a), (3a) to (9a), and (11a) for a nucleoside analog was also experimentally investigated. The results similar to in the case of introducing the nucleoside analogs (1;Ta) and (10;E) were obtained.

INDUSTRIAL APPLICABILITY

Since the activity is increased by introducing the nucleoside analog according to the present invention into a siRNA or a miRNA, application for the development of RNA drugs becomes possible. Furthermore, by introducing a nucleoside analog that introduces a photoreactive group, an mRNA can be captured. The photoreactive group reacts to light and provides active species capable of covalent bonding. Thus, the target of drug development can be explored.

A treatment method utilizing the oligonucleotide analog according to the present invention can be theoretically designed if the base sequence of a target gene or virus is apparent. Therefore, the treatment method can become a new approach to an intractable disease which has been considered difficult to be cured.

Also, the present invention can lead to elucidation of the gene control mechanism by an siRNA and a miRNA involved in RNA interference. Thus, the present invention can be utilized in the study for solving one of the most important problems to be solved in the life science field.

The invention claimed is:

1. A nucleoside analog or a salt thereof represented by any of general formulae (1) to (9):

[Chemical Formula 1]

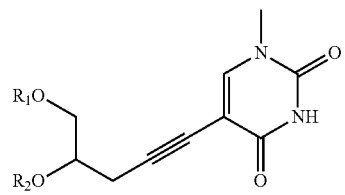

(1)

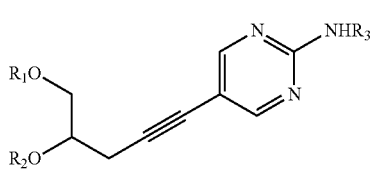

(2)

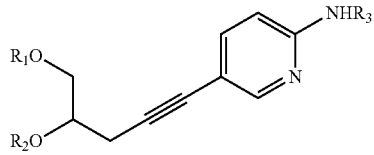

(3)

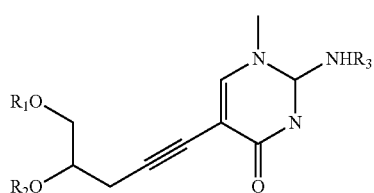

(4)

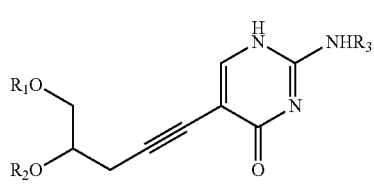

(5)

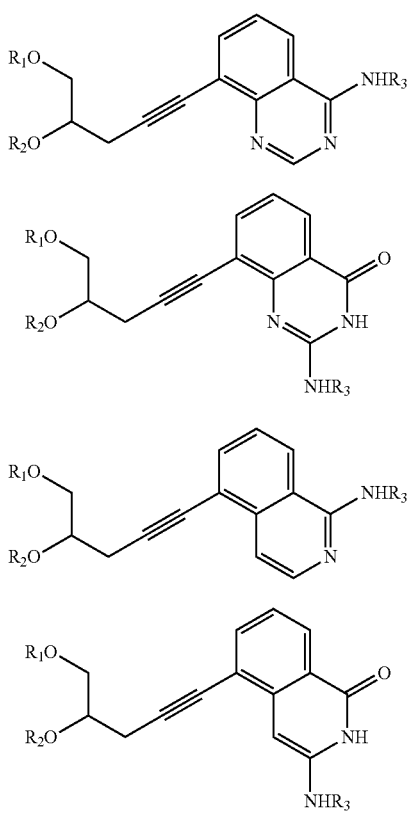

wherein $R_1$, $R_2$ and $R_3$ are the same or different groups, and each of the $R_1$, $R_2$ and $R_3$ is selected from: a hydrogen atom; a protecting group for a functional group in nucleic acid synthesis; and a phosphate group.

2. The nucleoside analog or the salt thereof according to claim 1,
wherein the $R_1$ is one of a hydrogen atom and a protecting group for a hydroxyl group that is the functional group in nucleic acid synthesis,
wherein the $R_2$ is selected from: a hydrogen atom; the protecting group for a hydroxyl group being a functional group in nucleic acid synthesis; and a phosphate group, and
wherein the $R_3$ is one of a hydrogen atom and a protecting group for an amino group that is the functional group in nucleic acid synthesis.

3. The nucleoside analog or the salt thereof according to claim 2,
wherein when each of the $R_1$ and the $R_2$ is the protecting group for a hydroxyl group that is the functional group in nucleic acid synthesis, the protecting group for a hydroxyl group that is the functional group in nucleic acid synthesis is selected from an aliphatic acyl group, an aromatic acyl group, an alkyoxy group, a methyl group substituted with an aryl group, a silyl group substituted with an aliphatic series, and a silyl group substituted with an aromatic series.

4. The nucleoside analog or the salt thereof according to claim 3,
wherein the aliphatic acyl group is an acetyl group,
wherein the aromatic acyl group is a benzoyl group,
wherein the methyl group substituted with an aryl group is selected from a benzyl group, a p-methoxybenzyl group, a 4,4'-dimethoxytrityl group and a 4-monomethoxytrityl group,
wherein the silyl group substituted with an aliphatic series is a tert-butyldimethylsilyl group, and
wherein the silyl group substituted with an aromatic series is a tert-butyldiphenylsilyl group.

5. The nucleoside analog or the salt thereof according to claim 2,
wherein when the $R_3$ is the protecting group for an amino group that is the functional group in nucleic acid synthesis, the protecting group for an amino group that is the functional group in nucleic acid synthesis is selected from an aliphatic acyl group, an aromatic acyl group, an alkyoxy group, a methyl group substituted with an aryl group, a silyl group substituted with an aliphatic series, a silyl group substituted with an aromatic series, a sulfonyl group substituted with an aliphatic series, a sulfonyl group substituted with an aromatic series, a carbonyl group, and an amide group.

6. The nucleoside analog or the salt thereof according to claim 5,
wherein the aliphatic acyl group is an acetyl group,
wherein the aromatic acyl group is a benzoyl group,
wherein the methyl group substituted with an aryl group is a benzyl group,
wherein the silyl group substituted with an aliphatic series is tert-butyldimethylsilyl group,
wherein the silyl group substituted with an aromatic series is tert-butyldiphenylsilyl group,
wherein the sulfonyl group substituted with an aromatic series is a p-toluenesulfonyl group,
wherein the carbonyl group is one of a tert-butoxycarbonyl group and a benzyloxy carbonyl group, and
wherein the amide group is one of a dimethylformamide group and a dimethylacetamide group.

7. The nucleoside analog or the salt thereof according to claim 1,
wherein the phosphate group includes:
a phosphate group protected by a protecting group in nucleic acid synthesis; and
an activated phosphate group for solid phase synthesis.

8. The nucleoside analog or the salt thereof according to claim 7,
wherein the phosphate group protected by a protecting group in nucleic acid synthesis is one of a 2-chlorophenylphosphate group and a 4-chlorophenylphosphate group.

9. The nucleoside analog or the salt thereof according to claim 7,
wherein the activated phosphate group for solid phase synthesis is one of —P(OC$_2$H$_4$CN)(N(CH(CH$_3$)$_2$)$_2$) and —P(OCH$_3$)(N(CH(CH$_3$)$_2$)$_2$).

10. A nucleoside analog or a salt thereof represented by a general formula (11) below:

[Chemical Formula 2]

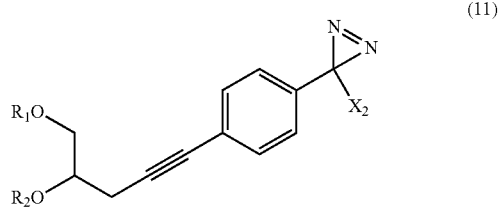

wherein R₁ and R₂ are the same or different groups, and each of the R₁ and R₂ is selected from: a hydrogen atom; a protecting group for a hydroxyl group in nucleic acid synthesis; and a phosphate group, wherein $X_2$ is an alkyl group or an alkyl group including at least one hydrogen substituted with halogen.

11. The nucleoside analog or the salt thereof according to claim 10 wherein the $X_2$ is selected from a trifluoromethyl group, a difluoromethyl group and a monofluoromethyl group.

12. The nucleoside analog or the salt thereof according to claim 10, wherein the R₁ is one of a hydrogen atom and a protecting group for a hydroxyl group in nucleic acid synthesis, wherein the R₂ is selected from: a hydrogen atom; a protecting group for a hydroxyl group in nucleic acid synthesis; and a phosphate group.

13. The nucleoside analog or the salt thereof according to claim 10, wherein the phosphate group includes:
a phosphate group protected by a protecting group in nucleic acid synthesis; and
an activated phosphate group for solid phase synthesis.

14. The nucleoside analog or the salt thereof according to claim 13, wherein the phosphate group protected by a protecting group in nucleic acid synthesis is one of a 2-chlorophenylphosphate group and a 4-chlorophenylphosphate group.

15. The nucleoside analog or the salt thereof according to claim 13, wherein the activated phosphate group for solid phase synthesis is one of —P(OC₂H₄CN)(N(CH(CH₃)₂)₂) and —P(OCH₃)(N(CH(CH₃)₂)₂).

16. An oligonucleotide analog containing one or more structures represented by any of formulae (1a) to (10a) as a component, wherein Ar is one of an aromatic hydrocarbon group or a polyaromatic hydrocarbon group:

[Chemical Formula 3]

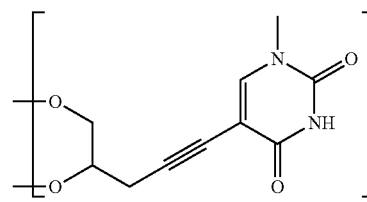

(1a)

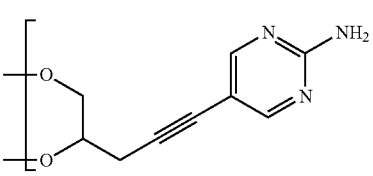

(2a)

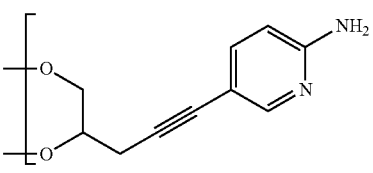

(3a)

-continued

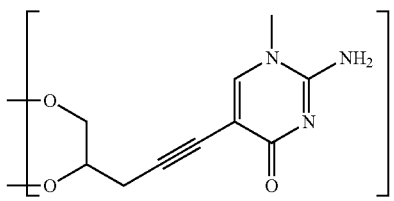

(4a)

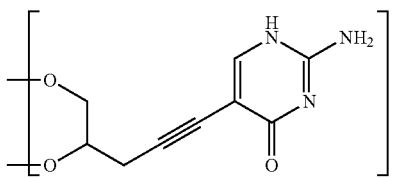

(5a)

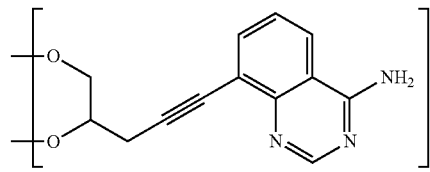

(6a)

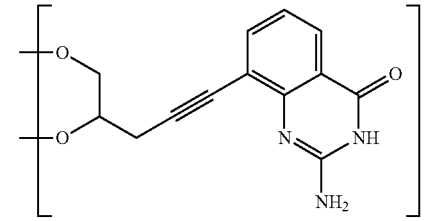

(7a)

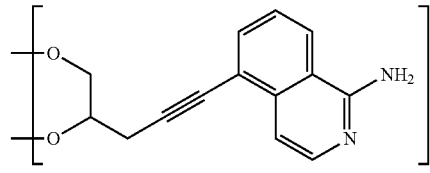

(8a)

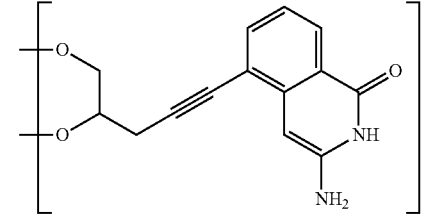

(9a)

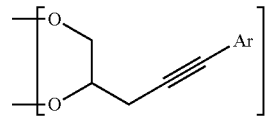

(10a)

17. An oligonucleotide analog containing one or more structures represented by a formula (11a) as a component:

[Chemical Formula 4]

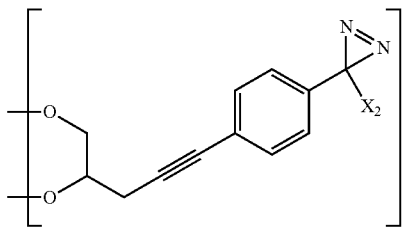

(11a)

wherein $X_2$ is an alkyl group or an alkyl group including at least one hydrogen substituted with halogen.

18. The oligonucleotide analog according to claim 17, wherein the $X_2$ is selected from a trifluoromethyl group, a difluoromethyl group and a monofluoromethyl group.

19. The oligonucleotide analog according to claim 16, wherein the oligonucleotide analog is formed one strand.

20. The oligonucleotide analog according to claim 16, wherein the oligonucleotide analog is formed a double strand with an oligonucleotide that contains an at least partially complementary sequence.

21. A nucleic-acid probe for detecting gene, comprising an oligonucleotide analog, the oligonucleotide analog containing one or more structures represented by a formula (11a) as a component:

[Chemical Formula 5]

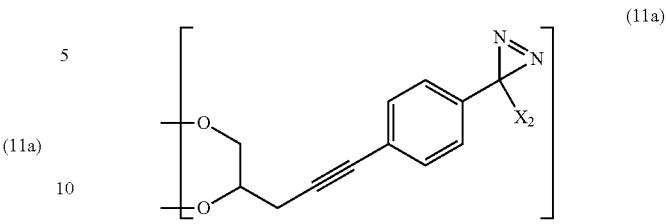

(11a)

wherein $X_2$ is an alkyl group or an alkyl group including at least one hydrogen substituted with halogen.

22. The oligonucleotide analog according to claim 17 wherein the oligonucleotide analog is formed one strand.

23. The oligonucleotide analog according to claim 17, wherein the oligonucleotide analog is formed a double strand with an oligonucleotide that contains an at least partially complementary sequence.

24. A gene expression inhibitor, comprising the oligonucleotide analog according to claim 16.

25. A gene expression inhibitor, comprising the oligonucleotide analog according to claim 17.

26. A gene expression inhibitor, comprising the oligonucleotide analog according to claim 18.

27. A gene expression inhibitor, comprising the oligonucleotide analog according to claim 22.

28. A gene expression inhibitor, comprising the oligonucleotide analog according to claim 19.

29. A gene expression inhibitor, comprising the oligonucleotide analog according to claim 20.

30. A gene expression inhibitor, comprising the oligonucleotide analog according to claim 23.

31. The nucleic-acid probe for detecting gene according to claim 21, wherein the $X_2$ is selected from a trifluoromethyl group, a difluoromethyl group and a monofluoromethyl group.

* * * * *

SEQUENCE LISTING

```
<160> NUMBER OF SEQ ID NOS: 69

<210> SEQ ID NO 1
<211> LENGTH: 10
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (1)..(10)
<223> OTHER INFORMATION: n at positions 1-10 stands for nucleoside
      analog(1)

<400> SEQUENCE: 1 nnnnnnnnnn                                                             10

<210> SEQ ID NO 2
<211> LENGTH: 10
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<223> OTHER INFORMATION: Thymidine polymer

<400> SEQUENCE: 2
tttttttttt                                                             10

<210> SEQ ID NO 3
<211> LENGTH: 10
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<223> OTHER INFORMATION: deoxyadenosine polymer

<400> SEQUENCE: 3
```
aaaaaaaaaa                                                                  10

<210> SEQ ID NO 4
<211> LENGTH: 10
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<223> OTHER INFORMATION: adenosine polymer

<400> SEQUENCE: 4
aaaaaaaaaa                                                                  10

<210> SEQ ID NO 5
<211> LENGTH: 18
<212> TYPE: RNA
<213> ORGANISM: Vargula
<220> FEATURE:
<223> OTHER INFORMATION: Firefly Luciferase

<400> SEQUENCE: 5
gaaggucaau guaucucu                                                         18

<210> SEQ ID NO 6
<211> LENGTH: 18
<212> TYPE: RNA
<213> ORGANISM: Vargula
<220> FEATURE:
<223> OTHER INFORMATION: Firefly Luciferase

<400> SEQUENCE: 6
gaaggucauu guaucucu                                                         18

<210> SEQ ID NO 7
<211> LENGTH: 18
<212> TYPE: RNA
<213> ORGANISM: Vargula
<220> FEATURE:
<223> OTHER INFORMATION: Firefly Luciferase

<400> SEQUENCE: 7
gaaggucacu guaucucu                                                         18

<210> SEQ ID NO 8
<211> LENGTH: 18
<212> TYPE: RNA
<213> ORGANISM: Vargula
<220> FEATURE:
<223> OTHER INFORMATION: Firefly Luciferase

<400> SEQUENCE: 8
gaaggucagu guaucucu                                                         18

<210> SEQ ID NO 9
<211> LENGTH: 18
<212> TYPE: RNA
<213> ORGANISM: Vargula
<220> FEATURE:
<223> OTHER INFORMATION: Firefly Luciferase

<400> SEQUENCE: 9
agagauacau ugaccuuc                                                         18

<210> SEQ ID NO 10

```
<211> LENGTH: 18
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(1)

<400> SEQUENCE: 10
agagauacan ugaccuuc                                                 18

<210> SEQ ID NO 11
<211> LENGTH: 18
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(11)
<223> OTHER INFORMATION: n at positions 10-11 n stands for nucleoside
      analog(1)

<400> SEQUENCE: 11
agagauacan ngaccuuc                                                 18

<210> SEQ ID NO 12
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(5)

<400> SEQUENCE: 12
gaaggtcaan gtatctct                                                 18

<210> SEQ ID NO 13
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(11)
<223> OTHER INFORMATION: n at positions 10-11 stands for nucleoside
      analog(5)

<400> SEQUENCE: 13
gaaggtcaan ntatctct                                                 18

<210> SEQ ID NO 14
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (9)..(11)
<223> OTHER INFORMATION: n at positions 9-11 stands for nucleoside
      analog(5)
```

```
<400> SEQUENCE: 14
gaaggtcann ntatctct                                                   18

<210> SEQ ID NO 15
<211> LENGTH: 18
<212> TYPE: DNA
<213> ORGANISM: Vargula
<220> FEATURE:
<223> OTHER INFORMATION: Firefly Luciferase

<400> SEQUENCE: 15
agagataggt tgaccttc                                                   18

<210> SEQ ID NO 16
<211> LENGTH: 18
<212> TYPE: DNA
<213> ORGANISM: Vargula
<220> FEATURE:
<223> OTHER INFORMATION: Firefly Luciferase

<400> SEQUENCE: 16 agagatoggg tgaccttc                                                   18

<210> SEQ ID NO 17
<211> LENGTH: 18
<212> TYPE: DNA
<213> ORGANISM: Vargula
<220> FEATURE:
<223> OTHER INFORMATION: Firefly Luciferase

<400> SEQUENCE: 17
gaaggtcaat gtatctct                                                   18

<210> SEQ ID NO 18
<211> LENGTH: 18
<212> TYPE: DNA
<213> ORGANISM: Vargula
<220> FEATURE:
<223> OTHER INFORMATION: Firefly Luciferase

<400> SEQUENCE: 18
agagatacat tgaccttc                                                   18

<210> SEQ ID NO 19
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(5)

<400> SEQUENCE: 19
gaaggtcaan gtatctct                                                   18

<210> SEQ ID NO 20
<211> LENGTH: 18
<212> TYPE: DNA
<213> ORGANISM: Vargula
<220> FEATURE:
<223> OTHER INFORMATION: Firefly Luciferase

<400> SEQUENCE: 20
```

-continued agagatacat tgaccttc                                       18

<210> SEQ ID NO 21
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(5)

<400> SEQUENCE: 21
gaaggtcaan gtatctct                                       18

<210> SEQ ID NO 22
<211> LENGTH: 18
<212> TYPE: DNA
<213> ORGANISM: Vargula
<220> FEATURE:
<223> OTHER INFORMATION: Firefly Luciferase

<400> SEQUENCE: 22
agagatacct tgaccttc                                       18

<210> SEQ ID NO 23
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(5)

<400> SEQUENCE: 23
gaaggtcaan gtatctct                                       18

<210> SEQ ID NO 24
<211> LENGTH: 18
<212> TYPE: DNA
<213> ORGANISM: Vargula
<220> FEATURE:
<223> OTHER INFORMATION: Firefly Luciferase

<400> SEQUENCE: 24
agagatactt tgaccttc                                       18

<210> SEQ ID NO 25
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(5)

<400> SEQUENCE: 25
gaaggtcaan gtatctct                                       18

<210> SEQ ID NO 26

```
<211> LENGTH: 18
<212> TYPE: DNA
<213> ORGANISM: Vargula
<220> FEATURE:
<223> OTHER INFORMATION: Firefly Luciferase

<400> SEQUENCE: 26
agagatacgt tgaccttc                                                 18

<210> SEQ ID NO 27
<211> LENGTH: 18
<212> TYPE: DNA
<213> ORGANISM: Vargula
<220> FEATURE:
<223> OTHER INFORMATION: Firefly Luciferase

<400> SEQUENCE: 27
gaaggtcaat gtatctct                                                 18

<210> SEQ ID NO 28
<211> LENGTH: 18
<212> TYPE: RNA
<213> ORGANISM: Vargula
<220> FEATURE:
<223> OTHER INFORMATION: Firefly Luciferase

<400> SEQUENCE: 28
agagauacau ugaccuuc                                                 18

<210> SEQ ID NO 29
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(5)

<400> SEQUENCE: 29
gaaggtcaan gtatctct                                                 18

<210> SEQ ID NO 30
<211> LENGTH: 18
<212> TYPE: RNA
<213> ORGANISM: Vargula
<220> FEATURE:
<223> OTHER INFORMATION: Firefly Luciferase

<400> SEQUENCE: 30
agagauacau ugaccuuc                                                 18

<210> SEQ ID NO 31
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(5)

<400> SEQUENCE: 31
gaaggtcaan gtatctct                                                 18
```

```
<210> SEQ ID NO 32
<211> LENGTH: 18
<212> TYPE: RNA
<213> ORGANISM: Vargula
<220> FEATURE:
<223> OTHER INFORMATION: Firefly Luciferase

<400> SEQUENCE: 32
agagauaccu ugaccuuc                                                 18

<210> SEQ ID NO 33
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(5)

<400> SEQUENCE: 33
gaaggtcaan gtatctct                                                 18

<210> SEQ ID NO 34
<211> LENGTH: 18
<212> TYPE: RNA
<213> ORGANISM: Vargula
<220> FEATURE:
<223> OTHER INFORMATION: Firefly Luciferase

<400> SEQUENCE: 34
agagauacuu ugaccuuc                                                 18

<210> SEQ ID NO 35
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(5)

<400> SEQUENCE: 35
gaaggtcaan gtatctct                                                 18

<210> SEQ ID NO 36
<211> LENGTH: 18
<212> TYPE: RNA
<213> ORGANISM: Vargula
<220> FEATURE:
<223> OTHER INFORMATION: Firefly Luciferase

<400> SEQUENCE: 36
agagauacgu ugaccuuc                                                 18

<210> SEQ ID NO 37
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
```

```
<221> NAME/KEY: misc_feature
<222> LOCATION: (10)..(11)
<223> OTHER INFORMATION: n at positions 10-11 stands for nucleoside
      analog(5)

<400> SEQUENCE: 37
gaaggtcaan ntatctct                                                   18

<210> SEQ ID NO 38
<211> LENGTH: 18
<212> TYPE: DNA
<213> ORGANISM: Vargula
<220> FEATURE:
<223> OTHER INFORMATION: Firefly Luciferase

<400> SEQUENCE: 38
agagataggt tgaccttc                                                   18

<210> SEQ ID NO 39
<211> LENGTH: 18
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (9)..(11)
<223> OTHER INFORMATION: n at positions 9-11 stands for nucleoside
      analog(5)

<400> SEQUENCE: 39
gaaggtcann ntatctct                                                   18

<210> SEQ ID NO 40
<211> LENGTH: 18
<212> TYPE: DNA
<213> ORGANISM: Vargula
<220> FEATURE:
<223> OTHER INFORMATION: Firefly Luciferase

<400> SEQUENCE: 40
agagataggg tgaccttc                                                   18

<210> SEQ ID NO 41
<211> LENGTH: 23
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (6)..(6)
<223> OTHER INFORMATION: n at positions 6-6 stands for nucleoside
      analog(1)

<400> SEQUENCE: 41
cccagnguuc agacuaccug uuc                                             23

<210> SEQ ID NO 42
<211> LENGTH: 23
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (9)..(9)
<223> OTHER INFORMATION: n at positions 9-9 stands for nucleoside
      analog(1)
```

```
<400> SEQUENCE: 42
cccagugunc agacuaccug uuc                                              23

<210> SEQ ID NO 43
<211> LENGTH: 23
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (15)..(15)
<223> OTHER INFORMATION: n at positions 15-15 stands for nucleoside
      analog(1)

<400> SEQUENCE: 43
cccaguguuc agacnaccug uuc                                              23

<210> SEQ ID NO 44
<211> LENGTH: 23
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (21)..(21)
<223> OTHER INFORMATION: n at positions 21-21 stands for nucleoside
      analog(1)

<400> SEQUENCE: 44
cccaguguuc agacuaccug nuc                                              23

<210> SEQ ID NO 45
<211> LENGTH: 22
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (17)..(17)
<223> OTHER INFORMATION: n at positions 17-17 stands for nucleoside
      analog(1)

<400> SEQUENCE: 45
acaguagucu gcacaunggu ua                                               22

<210> SEQ ID NO 46
<211> LENGTH: 22
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(1)

<400> SEQUENCE: 46
acaguagucn gcacauuggu ua                                               22

<210> SEQ ID NO 47
<211> LENGTH: 22
<212> TYPE: RNA
<213> ORGANISM: Artificial Sequence
<220> FEATURE:
```

```
<223> OTHER INFORMATION: Sequence is synthesized in the laboratory
<220> FEATURE:
<221> NAME/KEY: misc_feature
<222> LOCATION: (5)..(5)
<223> OTHER INFORMATION: n at positions 5-5 stands for nucleoside
      analog(1)
<220> FEATURE:
<221> NAME/KEY: misc_feature
<222> LOCATION: (17)..(17)
<223> OTHER INFORMATION: n at positions 17-17 stands for nucleoside
      analog(1)

<400> SEQUENCE: 47
acagnagucu gcacaunggu ua                                            22

<210> SEQ ID NO 48
<211> LENGTH: 23
<212> TYPE: RNA
<213> ORGANISM: Vargula
<220> FEATURE:
<223> OTHER INFORMATION: Firefly Luciferase

<400> SEQUENCE: 48
cccaguguuc agacuaccug uuc                                           23

<210> SEQ ID NO 49
<211> LENGTH: 22
<212> TYPE: RNA
<213> ORGANISM: Vargula
<220> FEATURE:
<223> OTHER INFORMATION: Firefly Luciferase

<400> SEQUENCE: 49
acaguagucu gcacauuggu ua                                            22

<210> SEQ ID NO 50
<211> LENGTH: 21
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (10)..(10)
<223> OTHER INFORMATION: n at positions 10-10 stands for nucleoside
      analog(10)

<400> SEQUENCE: 50
ugagguagun gguuguauag u                                             21

<210> SEQ ID NO 51
<211> LENGTH: 21
<212> TYPE: RNA
<213> ORGANISM: Vargula
<220> FEATURE:
<223> OTHER INFORMATION: Firefly Luciferase

<400> SEQUENCE: 51
acuauacaac cuacuaccuc a                                             21

<210> SEQ ID NO 52
<211> LENGTH: 21
<212> TYPE: RNA
<213> ORGANISM: Vargula
<220> FEATURE:
<223> OTHER INFORMATION: Firefly Luciferase

<400> SEQUENCE: 52
```
acuauacaaa cuacuaccuc a            21

<210> SEQ ID NO 53
<211> LENGTH: 21
<212> TYPE: RNA
<213> ORGANISM: Vargula
<220> FEATURE:
<223> OTHER INFORMATION: Firefly Luciferase

<400> SEQUENCE: 53
acaauacaac caacuaccuc a            21

<210> SEQ ID NO 54
<211> LENGTH: 21
<212> TYPE: DNA
<213> ORGANISM: Artificial Sequence
<220> FEATURE:
<223> OTHER INFORMATION: Sequence is synthesized in the laboratory
<220> FEATURE:
<223> OTHER INFORMATION: dangling end at 3'-terminal is thymidine
      RNA/DNA

<400> SEQUENCE: 54
cuucuucguc gagaccaugt t            21

<210> SEQ ID NO 55
<211> LENGTH: 21
<212> TYPE: DNA
<213> ORGANISM: Artificial Sequence
<220> FEATURE:
<223> OTHER INFORMATION: Sequence is synthesized in the laboratory
<220> FEATURE:
<223> OTHER INFORMATION: dangling end at 3'-terminal is thymidine
      RNA/DNA

<400> SEQUENCE: 55
cauggucucg acgaagaagt t            21

<210> SEQ ID NO 56
<211> LENGTH: 21
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (20)..(21)
<223> OTHER INFORMATION: n at positions 20-21 stands for nucleoside
      analog(1)

<400> SEQUENCE: 56
cuucuucguc gagaccaugn n            21

<210> SEQ ID NO 57
<211> LENGTH: 21
<212> TYPE: RNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (20)..(21)
<223> OTHER INFORMATION: n at positions 20-21 stands for nucleoside
      analog(1)

<400> SEQUENCE: 57
cauggucucg acgaagaagn n            21

```
<210> SEQ ID NO 58
<211> LENGTH: 21
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (2)..(2)
<223> OTHER INFORMATION: n at positions 2-2 stands for nucleoside
      analog(1) RNA/DNA
<220> FEATURE:
<223> OTHER INFORMATION: dangling end at 3'-terminal is thymidine
      RNA/DNA

<400> SEQUENCE: 58
cnucuucguc gagaccaugt t                                            21

<210> SEQ ID NO 59
<211> LENGTH: 21
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (18)..(18)
<223> OTHER INFORMATION: n at positions 18-18 stands for nucleoside
      analog(1) RNA/DNA
<220> FEATURE:
<223> OTHER INFORMATION: dangling end at 3'-terminal is thymidine
      RNA/DNA

<400> SEQUENCE: 59
cuucuucguc gagaccangt t                                            21

<210> SEQ ID NO 60
<211> LENGTH: 21
<212> TYPE: DNA
<213> ORGANISM: Vargula
<220> FEATURE:
<223> OTHER INFORMATION: dangling end at 3'-terminal is thymidine
      RNA/DNA
      Firefly Luciferase

<400> SEQUENCE: 60
cuucuucguc gagaccaugt t                                            21

<210> SEQ ID NO 61
<211> LENGTH: 21
<212> TYPE: DNA
<213> ORGANISM: Vargula
<220> FEATURE:
<223> OTHER INFORMATION: dangling end at 3'-terminal is thymidine
      RNA/DNA
      Firefly Luciferase

<400> SEQUENCE: 61
cauggucucg augaagaagt t                                            21

<210> SEQ ID NO 62
<211> LENGTH: 22
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (1)..(1)
<223> OTHER INFORMATION: n at positions 1-1 stands for nucleoside
      analog(100) RNA/DNA
```

```
<220> FEATURE:
<223> OTHER INFORMATION: dangling end at 3'-terminal is thymidine
      RNA/DNA

<400> SEQUENCE: 62
ncuucuucgu cgagaccaug tt                                                  22

<210> SEQ ID NO 63
<211> LENGTH: 22
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (1)..(1)
<223> OTHER INFORMATION: n at positions 1-1 stands for nucleoside
      analog(100) RNA/DNA
<220> FEATURE:
<223> OTHER INFORMATION: dangling end at 3'-terminal is thymidine
      RNA/DNA

<400> SEQUENCE: 63
ncauggucuc gaugaagaag tt                                                  22

<210> SEQ ID NO 64
<211> LENGTH: 21
<212> TYPE: DNA
<213> ORGANISM: Artificial Sequence
<220> FEATURE:
<223> OTHER INFORMATION: Sequence is synthesized in the laboratory
<220> FEATURE:
<223> OTHER INFORMATION: dangling end at 3'-terminal is thymidine
      RNA/DNA

<400> SEQUENCE: 64
cuucuucguc gagaccaugt t                                                   21

<210> SEQ ID NO 65
<211> LENGTH: 21
<212> TYPE: DNA
<213> ORGANISM: Vargula
<220> FEATURE:
<223> OTHER INFORMATION: dangling end at 3'-terminal is thymidine
      RNA/DNA
      Firefly Luciferase

<400> SEQUENCE: 65
cauggucucg augaagaagt t                                                   21

<210> SEQ ID NO 66
<211> LENGTH: 22
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (1)..(1)
<223> OTHER INFORMATION: n at positions 1-1 stands for nucleoside
      analog(100) RNA/DNA
<220> FEATURE:
<223> OTHER INFORMATION: dangling end at 3'-terminal is thymidine
      RNA/DNA

<400> SEQUENCE: 66
ncuucuucgu cgagaccaug tt                                                  22

<210> SEQ ID NO 67
```

```
<211> LENGTH: 21
<212> TYPE: DNA
<213> ORGANISM: Artificial Sequence
<220> FEATURE:
<223> OTHER INFORMATION: Sequence is synthesized in the laboratory
<220> FEATURE:
<223> OTHER INFORMATION: dangling end at 3'-terminal is thymidine
      RNA/DNA

<400> SEQUENCE: 67
cauggucucg augaagaagt t                                              21

<210> SEQ ID NO 68
<211> LENGTH: 21
<212> TYPE: DNA
<213> ORGANISM: Artificial Sequence
<220> FEATURE:
<223> OTHER INFORMATION: Sequence is synthesized in the laboratory
<220> FEATURE:
<223> OTHER INFORMATION: dangling end at 3'-terminal is thymidine
      RNA/DNA

<400> SEQUENCE: 68
cuucuucguc gagaccaugt t                                              21

<210> SEQ ID NO 69
<211> LENGTH: 22
<212> TYPE: DNA
<213> ORGANISM: Artificial Sequence
<220> FEATURE:
<223> OTHER INFORMATION: Sequence is synthesized in the laboratory
<220> FEATURE:
<221> NAME/KEY: misc_feature
<222> LOCATION: (1)..(1)
<223> OTHER INFORMATION: n at positions 1-1 stands for nucleoside
      analog(100) RNA/DNA
<220> FEATURE:
<223> OTHER INFORMATION: dangling end at 3'-terminal is thymidine
      RNA/DNA

<400> SEQUENCE: 69
ncauggucuc gaugaagaag tt                                             22
```